United States Patent [19]
Jin et al.

[11] Patent Number: 5,861,479
[45] Date of Patent: Jan. 19, 1999

[54] MORPHOGEN CELL SURFACE RECEPTOR

[75] Inventors: Donald F. Jin, Shrewsbury; Hermann Oppermann; Thangavel Kuberasampath, both of Medway; John E. Smart, Weston, all of Mass.

[73] Assignee: Creative BioMolecules, Inc., Hopkinton, Mass.

[21] Appl. No.: 459,009

[22] Filed: Jun. 2, 1995

Related U.S. Application Data

[62] Division of Ser. No. 357,533, Dec. 16, 1994, which is a continuation of Ser. No. 73,199, Jun. 7, 1993, abandoned.

[51] Int. Cl.[6] .......................... A61K 38/00; A61K 38/24; G01N 33/574; C12Q 1/68
[52] U.S. Cl. .......................... 530/324; 530/399; 435/7.23; 435/6; 536/23.51; 536/23.5; 536/24.33
[58] Field of Search ..................................... 435/7.2, 7.23, 435/6; 424/185.1; 530/399; 536/23.51, 23.5, 24.33

[56] References Cited

FOREIGN PATENT DOCUMENTS

WO92/20793  11/1992  WIPO .

*Primary Examiner*—Sheela Huff
*Assistant Examiner*—Yvonne Eyler
*Attorney, Agent, or Firm*—Testa, Hurwitz & Thibeault, LLP

[57] ABSTRACT

Disclosed are (1) nucleic acid sequences, amino acid sequences, homologies, structural features and various other data characterizing a morphogen cell surface receptor; (2) methods for producing receptor proteins, including fragments thereof, using recombinant DNA technology; (3) methods for identifying novel morphogen receptors and their encoding DNAs; (4) methods for identifying compounds capable of modulating endogenous morphogen receptor levels; and (5) methods for identifying morphogen receptor binding analogs useful in the design of morphogen agonists and antagonists for therapeutic, diagnostic and experimental uses.

7 Claims, 3 Drawing Sheets

```
MR-1       MSKYDLLYLTAHVTLVCCLIGIHG-------
ACTRII     MGAAAKLAFAVFLISCSS-------------
ACTRIIB    MTAPWAALALLWGSLCAG-------------
TGF-βRII   MGRGLLRGLWPLHIVLWTRIAST--------
daf-1      MRIRHVFCLLALVYG----------------
                    (25)
           ----------------SILPGSHGIIECEHF----DEKMCNTTQQCETRIEHCKMEADKFPSC
           ---------------------------------GAIL-GRSETQECLFFNANWERDRTNQTGV-----EPCYGDKDKRRHC
           ---------------------------------AGSGRGEAE-TRCIYYNANWELERTNQSGL------ERCEGEQDKRLHC
           -----------IPPHVQKSVNNDMIVTDNNGAVKFPQLCKFCDVRFS--TCDNQKSCMSNCSIT------SICEKPQEV----
           AETSDDDLDERTGIFIRDKLIPALKLAEVTKVNFTRLHLCHCSREVGCNARTTGWVPGIEFLNETDRSFYENT-CYTDG----SC YVLWSV---NETTGILRIKMKGCFTDMH-ECNQ-TECVTSAEPRQGNIHE-CCCKGSRC-NSNQKYIKSTTEATTQVPKEKTQDGSN
           FATWK----NISGSIEIVKQ-GCWLDDI-NCYDRTDC---IEKKDSPEVYE-CCCEGNMC-NEKFSYFPEMEVTQPTSNPVTPKPP
           YASWA----NSSGTIELVKK-GCWLDDF-NCYDRQEC---VATEENPQVYF-CCCEGNFC-NERFTHLPEPGGPEVTYE
           VAVMRKNDENITLETVCHDPKLPYHDFILEDAASPKGIMKEKKKPGETFFMCSCSSDEG-NDN-IIFSEEYNTSNPD
           YQSARPSPEISHFGCMDEKSVTDETEF---HDTAAKVC-TNNTKDPHATVWICCDKGNFCANET-IIHLAPGPQQSSTW
```

Fig. 2

```
                   ******** →#3503
(204)
MR-1     ELEQKASGREGDVWQAKEKN------QDVAVKIFRMQEKESWTTEHDIYKLPRMRHPNIIEFIGVEKHM--DKPEYW
ACTRII   LLEVKARGRFGCVWKAQLLN------EYVAVKIFPIQDKQSWQNEYEVYSLPGMKHENILQFIGAEKRGTSVDVDLW
ACTRIIB  ELEIKARGRFGCVWKAQMN-------DFVAVKIFPLQDKQSWQSEREIFSTPGMKHENILQFIAAEKRGSNLEVELW
TGF-βRII LDTLVGKGRFAEVYKAKLKQNTSEQFETVAVKIFPYEEYASWKDRKDIFSDINLKHENILQFLTAEERKTELGKQYW
daf-1    LTGFVGSGREGNVSRGDYRG------EAVAVKVFNALDEPAFHKETEIFETRMLRHPNVLRYIGSDRVDTGFVTELW
                                                     ******** →#3502
                                                   #3501→ ********
LLSTYQHNGSLCDYLKSHTIISWPELCRIAESMANGLAHLHEEIPASKTDGLKPSTAHRDFKSKNVLLKSDLTACIAD
ILTAFHEKGSLSDFLKANVVSWNELCHIAETMARGLAYLHEDIPGLK-DGHKPAISHRDIKSKNVLLKNNLTACIAD
LLTAFHDKGSITDYLKGNIITWNELCHVAETMSRGLSYLHEDVPWCRGEGHKPSTAHRDFKSKNVLLKSDLTAVLAD
LITAFHAKGNLQEYLTRHVISWEDLRNVGSSLARGLSHLHSDHTPC--GRPKMPIVHRDLKSSNILVKNDLTCCLCD
LVLEEYHPSGSLHDFLLENTVNIETYYNLMRSTASGLAFLHNQIGGSK-ESNKPAMAHRDIKSKNIMVKNDLTCAIGD

********
FGLAMIFQPGKPCGDT---HGQVGTRRYMAPEVLEGAINFNR-DAFLRIDVYACGLVLWEMVSRC--DFAGPVGEFQL
FGLALKFEAGKSAGDT---HGQVGTRRVMAPEVLEGAINFQR-DAFLRIDMYAMGLVLWELASRCTAADGPVDEYML
FGIAVRFEPGKPGDT----HGQVGTRRYMAPEVLEGAINFQR-DAFLRIDMYAMGLVLWELVSRCKAADGPVDEYML
FGISLRLGPYSSVDDLAN-SGQVGTARYMAPEVLESRMNLENAESFKQTDVYSMALVLWEMTSRCNAV-GEVKDYEP
LGLSLSKPEDAASDIIANENYKCGTVRVLAPEIENSTMQFTVFESYQCADVYSFSLVMMETLCRC--EDGDVLPREA
                    #3504→ ********
PFE------AELGLRPSLDEVQESVVMKKLRPRLLNSWRAHPGLNVFCDTMEECWDHDAEARLSSSCVMERFAQLNKYP
PFE------EEIGQHPSLEDMQEVVHKKKKRPVLRDYWQKHAGMAMLCETIEECWDHDAEARLSAGCVGERITQMQRLT
PFE------EEIGQHPSLEELQEVVHKKMRPTIKDHWLKHPGLAQLSVIIEECWDHDAEARLSAGCVEERVSLIRRSV
PE-------GSKVRDPVVESMKDNVLRD-RGTRNSSFWLNHQGIOMVCELLTECWDHDPEARLTAQCVAERFSELEHLD
ATVIPYIEWTDRDPQDAQMFDVVCTRRLRPTENPLWKDHPEMKHIMEIIKTCWNGNPSARFTSYICRKRMDERQQLL
                        (516)
STQLLIKNHTNIDDADESTNCL
NIITTEDIVTVVTMVTNVDFPPKESSL
NGTTSDCLVSLVTSVTNVDLLPKESSI
RLSGRSCSEEKIPEDGSLNTTK
LDKKAKAVAQTAGVTVQDRKILGGEKPKDESPANGAPRIVQKEIDREDEQENWRETAKTPNGHISSNDDSSRPLLG
```

Fig. 3

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 2625 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 379..1929
( D ) OTHER INFORMATION: /product="DROSOPHILA MORPHOGEN RECEPTOR"

( x i ) SEQUENCE DESCRIPTION: SEQ ID NO:1:

```
CACGAGAAAT  CGCTTGAAAA  CAGGCCCGCA  GACCTGCGAA  AAACGAAAAA  GTGCAGCGCG      60

CATATACTTT  TTCAACTGTG  CCCCTCTAGC  TTAAAATTAA  GTCGCGGCGA  AAAGTCGAGT     120

AAAAACCGCG  GAAATGCGCA  TGCAAACGGT  GTGTGGCCAG  CAAAATCGCT  GCCAAGGCAC     180

CGCACACACA  CTCGGCCACC  CACACATACA  CACTTAGTGC  TGTACTCGAA  AAGTGCGAAG     240

ACAACAGGAA  CTCTGTGCCA  AAATAATATT  AACAGTACCC  AGTTATTCCA  TTCCACTGCA     300

CCTGTCCCCG  AAACATCGAA  ATATTCGCGT  TACGTATACG  CAACGAGTGC  TGTAAACAAG     360

TTTGCACAGG  CGATAACA ATG TCC AAA TAC GAT CTG CTT TAT CTA ACG GCG           411
                     Met Ser Lys Tyr Asp Leu Leu Tyr Leu Thr Ala
                      1               5                      10

CAC GTA ACG CTG GTC TGC TGT CTG ATT GGA ATC CAT GGA TCT ATT TTG            459
His Val Thr Leu Val Cys Cys Leu Ile Gly Ile His Gly Ser Ile Leu
                 15                  20                  25

CCC GGA AGT CAT GGG ATC ATA GAA TGC GAG CAC TTC GAC GAG AAG ATG            507
Pro Gly Ser His Gly Ile Ile Glu Cys Glu His Phe Asp Glu Lys Met
             30                  35                  40

TGC AAC ACA ACG CAG CAA TGT GAA ACA CGG ATA GAG CAC TGT AAG ATG            555
Cys Asn Thr Thr Gln Gln Cys Glu Thr Arg Ile Glu His Cys Lys Met
         45                  50                  55

GAG GCG GAT AAG TTT CCC AGC TGC TAT GTC CTT TGG TCG GTC AAC GAG            603
Glu Ala Asp Lys Phe Pro Ser Cys Tyr Val Leu Trp Ser Val Asn Glu
 60                  65                  70                  75

ACA ACG GGC ATC CTG CGC ATC AAG ATG AAG GGC TGC TTC ACG GAC ATG            651
Thr Thr Gly Ile Leu Arg Ile Lys Met Lys Gly Cys Phe Thr Asp Met
                 80                  85                  90

CAC GAA TGC AAT CAG ACG GAG TGC GTG ACC AGT GCA GAG CCA CGG CAG            699
His Glu Cys Asn Gln Thr Glu Cys Val Thr Ser Ala Glu Pro Arg Gln
             95                 100                 105

GGA AAC ATT CAC TTC TGC TGC TGC AAG GGA TCG CGG TGC AAT TCC AAC            747
Gly Asn Ile His Phe Cys Cys Cys Lys Gly Ser Arg Cys Asn Ser Asn
         110                 115                 120

CAG AAA TAT ATT AAA AGC ACC ACG GAG GCA ACC ACA CAA GTG CCC AAG            795
Gln Lys Tyr Ile Lys Ser Thr Thr Glu Ala Thr Thr Gln Val Pro Lys
 125                 130                 135

GAG AAG ACG CAG GAC GGC AGC AAT TTG ATA TAC ATC TAC ATT GGC ACC            843
Glu Lys Thr Gln Asp Gly Ser Asn Leu Ile Tyr Ile Tyr Ile Gly Thr
 140                 145                 150                 155

TCC GTT TTC AGC GTG CTC ATG GTC ATT GTT GGC ATG GGC CTT CTT CTC            891
Ser Val Phe Ser Val Leu Met Val Ile Val Gly Met Gly Leu Leu Leu
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 160 |     |     |     |     |     | 165 |     |     |     |     | 170 |      |
| TAC | CGA | CGC | CGC | AAG | CAG | GCG | CAC | TTT | AAC | GAG | ATA | CCC | ACG | CAC | GAG | 939  |
| Tyr | Arg | Arg | Arg | Lys | Gln | Ala | His | Phe | Asn | Glu | Ile | Pro | Thr | His | Glu |      |
|     |     |     | 175 |     |     |     |     | 180 |     |     |     |     | 185 |     |     |      |
| GCT | GAG | ATA | ACA | AAC | TCA | TCG | CCA | TTG | CTC | AGC | AAC | CGT | CCC | ATT | CAG | 987  |
| Ala | Glu | Ile | Thr | Asn | Ser | Ser | Pro | Leu | Leu | Ser | Asn | Arg | Pro | Ile | Gln |      |
|     |     – 190 |     |     |     |     | 195 |     |     |     |     | 200 |     |     |     |      |
| CTG | CTG | GAA | CAG | AAG | GCC | AGT | GGT | AGA | TTC | GGT | GAT | GTG | TGG | CAA | GCC | 1035 |
| Leu | Leu | Glu | Gln | Lys | Ala | Ser | Gly | Arg | Phe | Gly | Asp | Val | Trp | Gln | Ala |      |
|     | 205 |     |     |     |     | 210 |     |     |     |     | 215 |     |     |     |     |      |
| AAG | CTC | AAC | AAT | CAG | GAT | GTG | GCC | GTC | AAG | ATC | TTT | CGC | ATG | CAG | GAA | 1083 |
| Lys | Leu | Asn | Asn | Gln | Asp | Val | Ala | Val | Lys | Ile | Phe | Arg | Met | Gln | Glu |      |
| 220 |     |     |     |     | 225 |     |     |     |     | 230 |     |     |     |     | 235 |      |
| AAA | GAA | TCG | TGG | ACC | ACG | GAG | CAC | GAT | ATC | TAC | AAG | CTG | CCG | CGC | ATG | 1131 |
| Lys | Glu | Ser | Trp | Thr | Thr | Glu | His | Asp | Ile | Tyr | Lys | Leu | Pro | Arg | Met |      |
|     |     |     |     | 240 |     |     |     |     | 245 |     |     |     |     | 250 |     |      |
| CGC | CAT | CCG | AAC | ATC | CTC | GAA | TTC | CTG | GGC | GTT | GAG | AAG | CAC | ATG | GAC | 1179 |
| Arg | His | Pro | Asn | Ile | Leu | Glu | Phe | Leu | Gly | Val | Glu | Lys | His | Met | Asp |      |
|     |     |     | 255 |     |     |     |     | 260 |     |     |     |     | 265 |     |     |      |
| AAG | CCG | GAA | TAT | TGG | CTG | ATA | TCC | ACC | TAC | CAG | CAT | AAC | GGA | TCA | CTA | 1227 |
| Lys | Pro | Glu | Tyr | Trp | Leu | Ile | Ser | Thr | Tyr | Gln | His | Asn | Gly | Ser | Leu |      |
|     |     | 270 |     |     |     |     | 275 |     |     |     |     | 280 |     |     |     |      |
| TGC | GAC | TAC | CTC | AAA | TCG | CAC | ACG | ATC | TCA | TGG | CCA | GAG | TTG | TGC | CGC | 1275 |
| Cys | Asp | Tyr | Leu | Lys | Ser | His | Thr | Ile | Ser | Trp | Pro | Glu | Leu | Cys | Arg |      |
|     | 285 |     |     |     |     | 290 |     |     |     |     | 295 |     |     |     |     |      |
| ATC | GCT | GAG | TCC | ATG | GCC | AAT | GGA | CTG | GCA | CAT | CTG | CAC | GAG | GAG | ATC | 1323 |
| Ile | Ala | Glu | Ser | Met | Ala | Asn | Gly | Leu | Ala | His | Leu | His | Glu | Glu | Ile |      |
| 300 |     |     |     |     | 305 |     |     |     |     | 310 |     |     |     |     | 315 |      |
| CCG | GCA | TCA | AAG | ACC | GAT | GGG | CTA | AAA | CCA | TCG | ATA | GCT | CAC | CGA | GAC | 1371 |
| Pro | Ala | Ser | Lys | Thr | Asp | Gly | Leu | Lys | Pro | Ser | Ile | Ala | His | Arg | Asp |      |
|     |     |     |     | 320 |     |     |     |     | 325 |     |     |     |     | 330 |     |      |
| TTC | AAG | TCT | AAG | AAC | GTA | CTG | CTT | AAG | AGC | GAT | CTG | ACG | GCC | TGT | ATA | 1419 |
| Phe | Lys | Ser | Lys | Asn | Val | Leu | Leu | Lys | Ser | Asp | Leu | Thr | Ala | Cys | Ile |      |
|     |     |     | 335 |     |     |     |     | 340 |     |     |     |     | 345 |     |     |      |
| GCT | GAC | TTT | GGT | TTG | GCC | ATG | ATA | TTC | CAG | CCA | GGC | AAG | CCC | TGC | GGC | 1467 |
| Ala | Asp | Phe | Gly | Leu | Ala | Met | Ile | Phe | Gln | Pro | Gly | Lys | Pro | Cys | Gly |      |
|     |     | 350 |     |     |     |     | 355 |     |     |     |     | 360 |     |     |     |      |
| GAT | ACA | CAC | GGT | CAA | GTA | GGC | ACT | CGA | CGT | TAC | ATG | GCC | CCA | GAG | GTG | 1515 |
| Asp | Thr | His | Gly | Gln | Val | Gly | Thr | Arg | Arg | Tyr | Met | Ala | Pro | Glu | Val |      |
|     | 365 |     |     |     |     | 370 |     |     |     |     | 375 |     |     |     |     |      |
| CTT | GAG | GGT | GCC | ATC | AAT | TTC | AAT | AGA | GAC | GCT | TTC | TTA | CGC | ATA | GAC | 1563 |
| Leu | Glu | Gly | Ala | Ile | Asn | Phe | Asn | Arg | Asp | Ala | Phe | Leu | Arg | Ile | Asp |      |
| 380 |     |     |     |     | 385 |     |     |     |     | 390 |     |     |     |     | 395 |      |
| GTC | TAC | GCA | TGC | GGC | CTA | GTC | CTC | TGG | GAA | ATG | GTG | TCA | CGG | TGT | GAC | 1611 |
| Val | Tyr | Ala | Cys | Gly | Leu | Val | Leu | Trp | Glu | Met | Val | Ser | Arg | Cys | Asp |      |
|     |     |     |     | 400 |     |     |     |     | 405 |     |     |     |     | 410 |     |      |
| TTT | GCC | GGA | CCC | GTC | GGT | GAG | TTC | CAG | CTG | CCT | TTT | GAG | GCC | GAG | CTG | 1659 |
| Phe | Ala | Gly | Pro | Val | Gly | Glu | Phe | Gln | Leu | Pro | Phe | Glu | Ala | Glu | Leu |      |
|     |     |     | 415 |     |     |     |     | 420 |     |     |     |     | 425 |     |     |      |
| GGC | CTG | AGG | CCG | TCG | CTG | GAC | GAA | GTT | CAG | GAG | AGT | GTG | GTA | ATG | AAG | 1707 |
| Gly | Leu | Arg | Pro | Ser | Leu | Asp | Glu | Val | Gln | Glu | Ser | Val | Val | Met | Lys |      |
|     |     | 430 |     |     |     |     | 435 |     |     |     |     | 440 |     |     |     |      |
| AAG | CTG | CGC | CCT | CGT | TTG | CTC | AAC | TCC | TGG | CGC | GCC | CAT | CCG | GGA | CTT | 1755 |
| Lys | Leu | Arg | Pro | Arg | Leu | Leu | Asn | Ser | Trp | Arg | Ala | His | Pro | Gly | Leu |      |
|     | 445 |     |     |     |     | 450 |     |     |     |     | 455 |     |     |     |     |      |
| AAT | GTA | TTC | TGC | GAC | ACA | ATG | GAG | GAG | TGC | TGG | GAT | CAC | GAC | GCT | GAG | 1803 |
| Asn | Val | Phe | Cys | Asp | Thr | Met | Glu | Glu | Cys | Trp | Asp | His | Asp | Ala | Glu |      |
| 460 |     |     |     |     | 465 |     |     |     |     | 470 |     |     |     |     | 475 |      |
| GCT | CGT | CTT | AGC | TCT | TCG | TGT | GTA | ATG | GAA | CGC | TTT | GCG | CAG | CTA | AAC | 1851 |
| Ala | Arg | Leu | Ser | Ser | Ser | Cys | Val | Met | Glu | Arg | Phe | Ala | Gln | Leu | Asn |      |

```
                              480                         485                          490
AAG  TAT  CCC  TCA  ACC  CAG  TTG  CTG  ATC  AAA  AAC  CAC  ACC  AAC  ATT  GAC          1899
Lys  Tyr  Pro  Ser  Thr  Gln  Leu  Leu  Ile  Lys  Asn  His  Thr  Asn  Ile  Asp
               495                         500                         505

GAC  GCC  AAG  GAA  TCT  ACG  AAT  TGC  TTA  TAGAAGCGGT  ACTAAGCCAC                      1946
Asp  Ala  Lys  Glu  Ser  Thr  Asn  Cys  Leu
          510                         515

AGACCAGCCA  GCGGATCTGT  GGCTCTGCAA  AAAAATCAGT  TGAAGCTTTT  TGCTTCGTAG                   2006

TGGATAGTTG  ATCGTCGAGG  TCGTAAGACG  TTTCGTTTGT  AGTTTAATAG  TTTGTAGTAC                   2066

CATTATAAGC  AGCTACAGAA  TGGGTTGATT  TATACGAAAG  AAGTCGTGTA  AGGTGTAACT                   2126

TTTCCTAAGG  GAAAAGCTAA  AAGCTTAACA  TGCCAACGAT  TTTTGTTAT   TATTTTCTTT                   2186

AAATTATAAA  TCGACTCATT  CGATGTTAAC  CCGAGATCTT  AAATCTGTTG  GAAATAAGTG                   2246

GAAACGTACA  CTAAGCAACT  TTGAACAAAG  AGCATTAGCT  ATGTCCAGAG  ACGTGGTAGT                   2306

TGCTAATCCG  ACATTGACTT  CATTGACTGA  TAACCATATA  TAGTTCTATA  TAAATCATGC                   2366

ATATAACGTA  CAATTTGTTT  TGCCCTCTGG  CAGTAGTCTG  TGTGCATATG  TAAACTGTTG                   2426

AAAATTATCG  TCAAGCCTTT  TAAAGTATAA  TTTTATTTGT  ACGTTATCGA  ATGTCTTCAT                   2486

ATAGTAGTAG  TTTTATATTT  AAAGTTATTT  TCAAAATAGA  TTTAACAATT  TTAGTTTACT                   2546

TTTTAGTTGT  AACGTTTTA   TTTCGCGCTC  AACGTGCAT   GCGTTTAAT   GTTGTATTTT                   2606

AAATAAAAAA  TACTTTAAA                                                                    2625
```

( 2 ) INFORMATION FOR SEQ ID NO:2:

( i ) SEQUENCE CHARACTERISTICS:
        ( A ) LENGTH: 516 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ser  Lys  Tyr  Asp  Leu  Leu  Tyr  Leu  Thr  Ala  His  Val  Thr  Leu  Val
 1                  5                         10                         15

Cys  Cys  Leu  Ile  Gly  Ile  His  Gly  Ser  Ile  Leu  Pro  Gly  Ser  His  Gly
               20                         25                         30

Ile  Ile  Glu  Cys  Glu  His  Phe  Asp  Glu  Lys  Met  Cys  Asn  Thr  Thr  Gln
          35                         40                         45

Gln  Cys  Glu  Thr  Arg  Ile  Glu  His  Cys  Lys  Met  Glu  Ala  Asp  Lys  Phe
     50                         55                         60

Pro  Ser  Cys  Tyr  Val  Leu  Trp  Ser  Val  Asn  Glu  Thr  Thr  Gly  Ile  Leu
 65                         70                         75                    80

Arg  Ile  Lys  Met  Lys  Gly  Cys  Phe  Thr  Asp  Met  His  Glu  Cys  Asn  Gln
               85                         90                         95

Thr  Glu  Cys  Val  Thr  Ser  Ala  Glu  Pro  Arg  Gln  Gly  Asn  Ile  His  Phe
              100                        105                        110

Cys  Cys  Cys  Lys  Gly  Ser  Arg  Cys  Asn  Ser  Asn  Gln  Lys  Tyr  Ile  Lys
              115                        120                        125

Ser  Thr  Thr  Glu  Ala  Thr  Thr  Gln  Val  Pro  Lys  Glu  Lys  Thr  Gln  Asp
     130                        135                        140

Gly  Ser  Asn  Leu  Ile  Tyr  Ile  Tyr  Ile  Gly  Thr  Ser  Val  Phe  Ser  Val
145                      150                        155                      160

Leu  Met  Val  Ile  Val  Gly  Met  Gly  Leu  Leu  Leu  Tyr  Arg  Arg  Arg  Lys
                    165                        170                        175

Gln  Ala  His  Phe  Asn  Glu  Ile  Pro  Thr  His  Glu  Ala  Glu  Ile  Thr  Asn
```

|     |     |     | 180 |     |     |     | 185 |     |     |     | 190 |     |     |
|-----|-----|-----|-----|-----|-----|-----|-----|-----|-----|-----|-----|-----|-----|

Ser Ser Pro Leu Leu Ser Asn Arg Pro Ile Gln Leu Leu Glu Gln Lys
        195                 200             205

Ala Ser Gly Arg Phe Gly Asp Val Trp Gln Ala Lys Leu Asn Asn Gln
    210             215             220

Asp Val Ala Val Lys Ile Phe Arg Met Gln Glu Lys Glu Ser Trp Thr
225             230             235                         240

Thr Glu His Asp Ile Tyr Lys Leu Pro Arg Met Arg His Pro Asn Ile
                245                 250             255

Leu Glu Phe Leu Gly Val Glu Lys His Met Asp Lys Pro Glu Tyr Trp
            260                 265             270

Leu Ile Ser Thr Tyr Gln His Asn Gly Ser Leu Cys Asp Tyr Leu Lys
        275                 280             285

Ser His Thr Ile Ser Trp Pro Glu Leu Cys Arg Ile Ala Glu Ser Met
    290                 295             300

Ala Asn Gly Leu Ala His Leu His Glu Glu Ile Pro Ala Ser Lys Thr
305                 310             315                     320

Asp Gly Leu Lys Pro Ser Ile Ala His Arg Asp Phe Lys Ser Lys Asn
            325                 330             335

Val Leu Leu Lys Ser Asp Leu Thr Ala Cys Ile Ala Asp Phe Gly Leu
        340                 345             350

Ala Met Ile Phe Gln Pro Gly Lys Pro Cys Gly Asp Thr His Gly Gln
        355                 360             365

Val Gly Thr Arg Arg Tyr Met Ala Pro Glu Val Leu Glu Gly Ala Ile
    370                 375             380

Asn Phe Asn Arg Asp Ala Phe Leu Arg Ile Asp Val Tyr Ala Cys Gly
385                 390             395                     400

Leu Val Leu Trp Glu Met Val Ser Arg Cys Asp Phe Ala Gly Pro Val
            405                 410             415

Gly Glu Phe Gln Leu Pro Phe Glu Ala Glu Leu Gly Leu Arg Pro Ser
            420                 425             430

Leu Asp Glu Val Gln Glu Ser Val Val Met Lys Lys Leu Arg Pro Arg
        435                 440             445

Leu Leu Asn Ser Trp Arg Ala His Pro Gly Leu Asn Val Phe Cys Asp
    450                 455             460

Thr Met Glu Glu Cys Trp Asp His Asp Ala Glu Ala Arg Leu Ser Ser
465                 470             475                     480

Ser Cys Val Met Glu Arg Phe Ala Gln Leu Asn Lys Tyr Pro Ser Thr
            485                 490             495

Gln Leu Leu Ile Lys Asn His Thr Asn Ile Asp Asp Ala Lys Glu Ser
        500                 505             510

Thr Asn Cys Leu
        515

( 2 ) INFORMATION FOR SEQ ID NO:3:

( i ) SEQUENCE CHARACTERISTICS:
            ( A ) LENGTH: 194 base pairs
            ( B ) TYPE: nucleic acid
            ( C ) STRANDEDNESS: single
            ( D ) TOPOLOGY: linear ( i i ) MOLECULE TYPE: DNA (genomic)

( i x ) FEATURE:
            ( A ) NAME/KEY: misc_feature
            ( B ) LOCATION: 1..194
            ( D ) OTHER INFORMATION: /product="DROSOPHILA GENOMIC DNA

PROBE USED TO CLONE RECEPTOR CDNA"

(x i) SEQUENCE DESCRIPTION: SEQ ID NO:3:

| | | | | | |
|---|---|---|---|---|---|
| GAATCTGTGG | CAGTGAAAAT | CTTCCCGCAT | GCAGGAAAAA | GAATCGTGGA | CCACGGAGCA | 60
| CGATATCTAC | AAGCTGCCGC | GCATGGCCAT | CCGAACATCC | TCGAATTCCT | GGGCGTTGAG | 120
| AAGCACATGG | ACAAGCCGGA | ATATTGGCTG | ATATCCACCT | ACCAGCATAA | CGGTATCACT | 180
| ATGCGTCTTC | CTAG | | | | | 194

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (i x) FEATURE:
        (A) NAME/KEY: misc_feature
        (B) LOCATION: 1..24
        (D) OTHER INFORMATION: /product="PRIMER 1"

(x i) SEQUENCE DESCRIPTION: SEQ ID NO:4:

ATTSKWRCTY TTGADGTCSC KGTG        24

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: cDNA (i x) FEATURE:
        (A) NAME/KEY: misc_feature
        (B) LOCATION: 1..23
        (D) OTHER INFORMATION: /product="PRIMER 2"

(x i) SEQUENCE DESCRIPTION: SEQ ID NO:5:

ATYGCBCACM GSGAYHTCAA RAG        23

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (i i) MOLECULE TYPE: cDNA (i x) FEATURE:
        (A) NAME/KEY: misc_feature
        (B) LOCATION: 1..26
        (D) OTHER INFORMATION: /product="PRIMER 3"

(x i) SEQUENCE DESCRIPTION: SEQ ID NO:6:

GAATCTGTSG CHGTSAARRT HTTYCC        26

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: cDNA (i x) FEATURE:
    (A) NAME/KEY: misc_feature
    (B) LOCATION: 1..23
    (D) OTHER INFORMATION: /product="PRIMER 4"

(x i) SEQUENCE DESCRIPTION: SEQ ID NO:7:

TCCAGSACYT CNGGDGCCAK RTA    23

(2) INFORMATION FOR SEQ ID NO:8:

(i) SEQUENCE CHARACTERISTICS:
        (A) LENGTH: 669 amino acids
        (B) TYPE: amino acid
        (C) STRANDEDNESS: single
        (D) TOPOLOGY: linear (i i) MOLECULE TYPE: protein (i x) FEATURE:
        (A) NAME/KEY: Protein
        (B) LOCATION: 1..669
        (D) OTHER INFORMATION: /note= "C ELEGANS RECEPTOR KINASE"

(x i) SEQUENCE DESCRIPTION: SEQ ID NO:8:

```
Met Arg Ile Arg His Val Val Phe Cys Leu Leu Ala Leu Val Tyr Gly
 1               5                  10                  15

Ala Glu Thr Ser Asp Asp Leu Asp Glu Arg Thr Asn Ile Phe Ile
            20                  25                  30

Arg Asp Lys Leu Ile Pro Ala Leu Lys Leu Ala Glu Val Thr Lys Val
            35                  40                  45

Asn Phe Thr Arg Leu His Leu Cys His Cys Ser Arg Glu Val Gly Cys
 50                  55                  60

Asn Ala Arg Thr Thr Gly Trp Val Pro Gly Ile Glu Phe Leu Asn Glu
 65                  70                  75                  80

Thr Asp Arg Ser Phe Tyr Glu Asn Thr Cys Tyr Thr Asp Gly Ser Cys
                85                  90                  95

Tyr Gln Ser Ala Arg Pro Ser Pro Glu Ile Ser His Phe Gly Cys Met
                100                 105                 110

Asp Glu Lys Ser Val Thr Asp Glu Thr Glu Phe His Asp Thr Ala Ala
            115                 120                 125

Lys Val Cys Thr Asn Asn Thr Lys Asp Pro His Ala Thr Val Trp Ile
    130                 135                 140

Cys Cys Asp Lys Gly Asn Phe Cys Ala Asn Glu Thr Ile Ile His Leu
145                 150                 155                 160

Ala Pro Gly Pro Gln Gln Ser Ser Thr Trp Leu Ile Leu Thr Ile Leu
                165                 170                 175

Ala Leu Leu Thr Phe Ile Val Leu Leu Gly Ile Ala Ile Phe Leu Thr
            180                 185                 190

Arg Lys Ser Trp Glu Ala Lys Phe Asp Trp Tyr Ile Arg Phe Lys Pro
            195                 200                 205

Lys Pro Gly Asp Pro Leu Arg Glu Thr Glu Asn Asn Val Pro Met Val
    210                 215                 220

Thr Met Gly Asp Gly Ala Gly Ser Ser Val Pro Glu Val Ala Pro Ile
225                 230                 235                 240

Glu Gln Gln Gly Ser Thr Met Ser Thr Ser Ala Gly Asn Ser Phe Pro
                245                 250                 255

Pro Gly Ile Met Pro Asn Asn Met Lys Asp Met Leu Asp Val Leu Glu
            260                 265                 270
```

```
Glu Thr Ser Gly Ser Gly Met Gly Pro Thr Thr Leu His Lys Leu Thr
        275             280                 285
Ile Gly Gly Gln Ile Arg Leu Thr Gly Arg Val Gly Ser Gly Arg Phe
    290             295             300
Gly Asn Val Ser Arg Gly Asp Tyr Arg Gly Glu Ala Val Ala Val Lys
305             310             315                         320
Val Phe Asn Ala Leu Asp Glu Pro Ala Phe His Lys Glu Thr Glu Ile
                325             330                         335
Phe Glu Thr Arg Met Leu Arg His Pro Asn Val Leu Arg Tyr Ile Gly
            340             345                 350
Ser Asp Arg Val Asp Thr Gly Phe Val Thr Glu Leu Trp Leu Val Thr
            355             360             365
Glu Tyr His Pro Ser Gly Ser Leu His Asp Phe Leu Leu Glu Asn Thr
    370             375                 380
Val Asn Ile Glu Thr Tyr Tyr Asn Leu Met Arg Ser Thr Ala Ser Gly
385                 390             395                     400
Leu Ala Phe Leu His Asn Gln Ile Gly Gly Ser Lys Glu Ser Asn Lys
                405             410             415
Pro Ala Met Ala His Arg Asp Ile Lys Ser Lys Asn Ile Met Val Lys
            420             425             430
Asn Asp Leu Thr Cys Ala Ile Gly Asp Leu Gly Leu Ser Leu Ser Lys
        435             440             445
Pro Glu Asp Ala Ala Ser Asp Ile Ile Ala Asn Glu Asn Tyr Lys Cys
        450             455             460
Gly Thr Val Arg Tyr Leu Ala Pro Glu Ile Leu Asn Ser Thr Met Gln
465             470             475                     480
Phe Thr Val Phe Glu Ser Tyr Gln Cys Ala Asp Val Tyr Ser Phe Ser
                485             490                 495
Leu Val Met Trp Glu Thr Leu Cys Arg Cys Glu Asp Gly Asp Val Leu
            500             505             510
Pro Arg Glu Ala Ala Thr Val Ile Pro Tyr Ile Glu Trp Thr Asp Arg
        515             520             525
Asp Pro Gln Asp Ala Gln Met Phe Asp Val Val Cys Thr Arg Arg Leu
    530             535             540
Arg Pro Thr Glu Asn Pro Leu Trp Lys Asp His Pro Glu Met Lys His
545             550             555                     560
Ile Met Glu Ile Ile Lys Thr Cys Trp Asn Gly Asn Pro Ser Ala Arg
                565             570             575
Phe Thr Ser Tyr Ile Cys Arg Lys Arg Met Asp Glu Arg Gln Gln Leu
            580             585             590
Leu Leu Asp Lys Lys Ala Lys Ala Val Ala Gln Thr Ala Gly Val Thr
        595             600             605
Val Gln Asp Arg Lys Ile Leu Gly Pro Gln Lys Pro Lys Asp Glu Ser
    610             615             620
Pro Ala Asn Gly Ala Pro Arg Ile Val Gln Lys Glu Ile Asp Arg Glu
625             630             635                     640
Asp Glu Gln Glu Asn Trp Arg Glu Thr Ala Lys Thr Pro Asn Gly His
                645             650             655
Ile Ser Ser Asn Asp Asp Ser Ser Arg Pro Leu Leu Gly
            660             665
```

( 2 ) INFORMATION FOR SEQ ID NO:9:

( i ) SEQUENCE CHARACTERISTICS:

(A) LENGTH: 565 amino acids
(B) TYPE: amino acid
(C) STRANDEDNESS: single
(D) TOPOLOGY: linear (ii) MOLECULE TYPE: protein (ix) FEATURE:
(A) NAME/KEY: Protein
(B) LOCATION: 1..565
(D) OTHER INFORMATION: /note= "TGF-B TYPE II RECEPTOR"

(xi) SEQUENCE DESCRIPTION: SEQ ID NO:9:

```
Met Gly Arg Gly Leu Leu Arg Gly Leu Trp Pro Leu His Ile Val Leu
 1               5                  10                  15

Trp Thr Arg Ile Ala Ser Thr Ile Pro Pro His Val Gln Lys Ser Val
            20                  25                  30

Asn Asn Asp Met Ile Val Thr Asp Asn Gly Ala Val Lys Phe Pro
            35              40                  45

Gln Leu Cys Lys Phe Cys Asp Val Arg Phe Ser Thr Cys Asp Asn Gln
        50              55                  60

Lys Ser Cys Met Ser Asn Cys Ser Ile Thr Ser Ile Cys Glu Lys Pro
 65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
            115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
            180                 185                 190

Arg Gln Gln Lys Leu Ser Ser Thr Trp Glu Thr Gly Lys Thr Arg Lys
        195                 200                 205

Leu Met Glu Phe Ser Glu His Cys Ala Ile Ile Leu Glu Asp Asp Arg
    210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ala Ser Trp Lys
        275                 280                 285

Asp Arg Lys Asp Ile Phe Ser Asp Ile Asn Leu Lys His Glu Asn Ile
    290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Asn Val Gly Ser
            340                 345                 350
```

Ser Leu Ala Arg Gly Leu Ser His Leu His Ser Asp His Thr Pro Cys
355                 360             365

Gly Arg Pro Lys Met Pro Ile Val His Arg Asp Leu Lys Ser Ser Asn
370             375             380

Ile Leu Val Lys Asn Asp Leu Thr Cys Cys Leu Cys Asp Phe Gly Leu
385             390             395             400

Ser Leu Arg Leu Gly Pro Tyr Ser Ser Val Asp Asp Leu Ala Asn Ser
            405             410             415

Gly Gln Val Gly Thr Ala Arg Tyr Met Ala Pro Glu Val Leu Glu Ser
            420             425             430

Arg Met Asn Leu Glu Asn Ala Glu Ser Phe Lys Gln Thr Asp Val Tyr
        435             440             445

Ser Met Ala Leu Val Leu Trp Glu Met Thr Ser Arg Cys Asn Ala Val
    450             455             460

Gly Glu Val Lys Asp Tyr Glu Pro Pro Phe Gly Ser Lys Val Arg Asp
465             470             475             480

Pro Val Val Glu Ser Met Lys Asp Asn Val Leu Arg Asp Arg Gly Thr
            485             490             495

Arg Asn Ser Ser Phe Trp Leu Asn His Gln Gly Ile Gln Met Val Cys
            500             505             510

Glu Thr Leu Thr Glu Cys Trp Asp His Asp Pro Glu Ala Arg Leu Thr
        515             520             525

Ala Gln Cys Val Ala Glu Arg Phe Ser Glu Leu Glu His Leu Asp Arg
    530             535             540

Leu Ser Gly Arg Ser Cys Ser Glu Glu Lys Ile Pro Glu Asp Gly Ser
545             550             555             560

Leu Asn Thr Thr Lys
            565

( 2 ) INFORMATION FOR SEQ ID NO:10:

( i ) SEQUENCE CHARACTERISTICS:
        ( A ) LENGTH: 513 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..513
        ( D ) OTHER INFORMATION: /note= "MOUSE ACTIVIN RECEPTOR"

( x i ) SEQUENCE DESCRIPTION: SEQ ID NO:10:

Met Gly Ala Ala Ala Lys Leu Ala Phe Ala Val Phe Leu Ile Ser Cys
1               5               10              15

Ser Ser Gly Ala Ile Leu Gly Arg Ser Glu Thr Gln Glu Cys Leu Phe
            20              25              30

Phe Asn Ala Asn Trp Glu Arg Asp Arg Thr Asn Gln Thr Gly Val Glu
        35              40              45

Pro Cys Tyr Gly Asp Lys Asp Lys Arg Arg His Cys Phe Ala Thr Trp
    50              55              60

Lys Asn Ile Ser Gly Ser Ile Glu Ile Val Lys Gln Gly Cys Trp Leu
65              70              75              80

Asp Asp Ile Asn Cys Tyr Asp Arg Thr Asp Cys Ile Glu Lys Lys Asp
            85              90              95

Ser Pro Glu Val Tyr Phe Cys Cys Cys Glu Gly Asn Met Cys Asn Glu
            100             105             110

-continued

```
Lys Phe Ser Tyr Phe Pro Glu Met Glu Val Thr Gln Pro Thr Ser Asn
            115             120             125

Pro Val Thr Pro Lys Pro Pro Tyr Tyr Asn Ile Leu Leu Tyr Ser Leu
    130             135             140

Val Pro Leu Met Leu Ile Ala Gly Ile Val Ile Cys Ala Phe Trp Val
145             150             155                         160

Tyr Arg His His Lys Met Ala Tyr Pro Pro Val Leu Val Pro Thr Gln
                165             170                     175

Asp Pro Gly Pro Pro Pro Ser Pro Leu Leu Gly Leu Lys Pro Leu
            180             185             190

Gln Leu Leu Glu Val Lys Ala Arg Gly Arg Phe Gly Cys Val Trp Lys
    195             200             205

Ala Gln Leu Leu Asn Glu Tyr Val Ala Val Lys Ile Phe Pro Ile Gln
    210             215             220

Asp Lys Gln Ser Trp Gln Asn Glu Tyr Glu Val Tyr Ser Leu Pro Gly
225             230             235                         240

Met Lys His Glu Asn Ile Leu Gln Phe Ile Gly Ala Glu Lys Arg Gly
                245             250             255

Thr Ser Val Asp Val Asp Leu Trp Leu Ile Thr Ala Phe His Glu Lys
            260             265             270

Gly Ser Leu Ser Asp Phe Leu Lys Ala Asn Val Val Ser Trp Asn Glu
            275             280             285

Leu Cys His Ile Ala Glu Thr Met Ala Arg Gly Leu Ala Tyr Leu His
    290             295             300

Glu Asp Ile Pro Gly Leu Lys Asp Gly His Lys Pro Ala Ile Ser His
305             310             315                         320

Arg Asp Ile Lys Ser Lys Asn Val Leu Leu Lys Asn Asn Leu Thr Ala
                325             330             335

Cys Ile Ala Asp Phe Gly Leu Ala Leu Lys Phe Glu Ala Gly Lys Ser
            340             345             350

Ala Gly Asp Thr His Gly Gln Val Gly Thr Arg Arg Tyr Met Ala Pro
            355             360             365

Glu Val Leu Glu Gly Ala Ile Asn Phe Gln Arg Asp Ala Phe Leu Arg
    370             375             380

Ile Asp Met Tyr Ala Met Gly Leu Val Leu Trp Glu Leu Ala Ser Arg
385             390             395                         400

Cys Thr Ala Ala Asp Gly Pro Val Asp Glu Tyr Met Leu Pro Phe Glu
            405             410             415

Glu Glu Ile Gly Gln His Pro Ser Leu Glu Asp Met Gln Glu Val Val
            420             425             430

Val His Lys Lys Lys Arg Pro Val Leu Arg Asp Tyr Trp Gln Lys His
        435             440             445

Ala Gly Met Ala Met Leu Cys Glu Thr Ile Glu Glu Cys Trp Asp His
    450             455             460

Asp Ala Glu Ala Arg Leu Ser Ala Gly Cys Val Gly Glu Arg Ile Thr
465             470             475                         480

Gln Met Gln Arg Leu Thr Asn Ile Ile Thr Thr Glu Asp Ile Val Thr
            485             490             495

Val Val Thr Met Val Thr Asn Val Asp Phe Pro Pro Lys Glu Ser Ser
            500             505             510

Leu
```

( 2 ) INFORMATION FOR SEQ ID NO:11:

( i ) SEQUENCE CHARACTERISTICS:
  ( A ) LENGTH: 513 amino acids
  ( B ) TYPE: amino acid
  ( C ) STRANDEDNESS: single
  ( D ) TOPOLOGY: linear ( i i ) MOLECULE TYPE: protein ( i x ) FEATURE:
  ( A ) NAME/KEY: Protein
  ( B ) LOCATION: 1..513
  ( D ) OTHER INFORMATION: /note= "RAT ACTIVIN TYPE II RECEPTOR"

( x i ) SEQUENCE DESCRIPTION: SEQ ID NO:11:

| | | | | | | | | | | | | | | |
|---|---|---|---|---|---|---|---|---|---|---|---|---|---|---|
| Met | Thr | Ala | Pro | Trp | Ala | Ala | Leu | Ala | Leu | Leu | Trp | Gly | Ser | Leu | Cys |
| 1 | | | | 5 | | | | | 10 | | | | | 15 | |
| Ala | Gly | Ser | Gly | Arg | Gly | Glu | Ala | Glu | Thr | Arg | Glu | Cys | Ile | Tyr | Tyr |
| | | | 20 | | | | | 25 | | | | | 30 | | |
| Asn | Ala | Asn | Trp | Glu | Leu | Glu | Arg | Thr | Asn | Gln | Ser | Gly | Leu | Glu | Arg |
| | | | 35 | | | | 40 | | | | | 45 | | | |
| Cys | Glu | Gly | Glu | Gln | Asp | Lys | Arg | Leu | His | Cys | Tyr | Ala | Ser | Trp | Pro |
| | | | 50 | | | | 55 | | | | | 60 | | | |
| Asn | Ser | Ser | Gly | Thr | Ile | Glu | Leu | Val | Lys | Lys | Gly | Cys | Trp | Leu | Asp |
| 65 | | | | | 70 | | | | | 75 | | | | | 80 |
| Asp | Phe | Asn | Cys | Tyr | Asp | Arg | Gln | Glu | Cys | Val | Ala | Thr | Glu | Glu | Asn |
| | | | | 85 | | | | | 90 | | | | | 95 | |
| Pro | Gln | Val | Tyr | Phe | Cys | Cys | Cys | Glu | Gly | Asn | Phe | Cys | Asn | Glu | Arg |
| | | | 100 | | | | | 105 | | | | | 110 | | |
| Phe | Thr | His | Leu | Pro | Glu | Pro | Gly | Gly | Pro | Glu | Val | Thr | Tyr | Glu | Pro |
| | | | 115 | | | | | 120 | | | | | 125 | | |
| Pro | Pro | Thr | Ala | Pro | Thr | Leu | Leu | Thr | Val | Leu | Ala | Tyr | Ser | Leu | Leu |
| | | 130 | | | | | 135 | | | | | 140 | | | |
| Pro | Ile | Gly | Gly | Leu | Ser | Leu | Ile | Val | Leu | Leu | Ala | Phe | Trp | Met | Tyr |
| 145 | | | | | 150 | | | | | 155 | | | | | 160 |
| Arg | His | Arg | Lys | Pro | Pro | Tyr | Gly | His | Val | Asp | Ile | His | Glu | Asp | Pro |
| | | | | 165 | | | | | 170 | | | | | 175 | |
| Gly | Pro | Pro | Pro | Pro | Ser | Pro | Leu | Val | Gly | Leu | Lys | Pro | Leu | Gln | Leu |
| | | | 180 | | | | | 185 | | | | | 190 | | |
| Leu | Glu | Ile | Lys | Ala | Arg | Gly | Arg | Phe | Gly | Cys | Val | Trp | Lys | Ala | Gln |
| | | 195 | | | | | 200 | | | | | 205 | | | |
| Leu | Met | Asn | Asp | Phe | Val | Ala | Val | Lys | Ile | Phe | Pro | Leu | Gln | Asp | Lys |
| | 210 | | | | | 215 | | | | | 220 | | | | |
| Gln | Ser | Trp | Gln | Ser | Glu | Arg | Glu | Ile | Phe | Ser | Thr | Pro | Gly | Met | Lys |
| 225 | | | | | 230 | | | | | 235 | | | | | 240 |
| His | Glu | Asn | Leu | Leu | Gln | Phe | Ile | Ala | Ala | Glu | Lys | Arg | Gly | Cys | Ser |
| | | | | 245 | | | | | 250 | | | | | 255 | |
| Asn | Leu | Glu | Val | Glu | Leu | Trp | Leu | Ile | Thr | Ala | Phe | His | Asp | Lys | Gly |
| | | | 260 | | | | | 265 | | | | | 270 | | |
| Ser | Leu | Thr | Asp | Tyr | Leu | Lys | Gly | Asn | Ile | Ile | Thr | Trp | Asn | Glu | Leu |
| | | 275 | | | | | 280 | | | | | 285 | | | |
| Cys | His | Val | Ala | Glu | Thr | Met | Ser | Arg | Gly | Leu | Ser | Tyr | Leu | His | Glu |
| | 290 | | | | | 295 | | | | | 300 | | | | |
| Asp | Val | Pro | Trp | Cys | Arg | Gly | Glu | Gly | His | Lys | Pro | Ser | Ile | Ala | His |
| 305 | | | | | 310 | | | | | 315 | | | | | 320 |
| Arg | Asp | Phe | Lys | Ser | Lys | Asn | Val | Leu | Leu | Lys | Ser | Asp | Leu | Thr | Ala |
| | | | | 325 | | | | | 330 | | | | | 335 | |

|     |     |     |     |     |     |     |     |     |     |     |     |     |     |     |
| --- | --- | --- | --- | --- | --- | --- | --- | --- | --- | --- | --- | --- | --- | --- |
| Val | Leu | Ala | Asp<br>340 | Phe | Gly | Leu | Ala | Val<br>345 | Arg | Phe | Glu | Pro | Gly<br>350 | Lys | Pro |
| Pro | Gly | Asp<br>355 | Thr | His | Gly | Gln | Val<br>360 | Gly | Thr | Arg | Arg<br>365 | Tyr | Met | Ala | Pro |
| Glu | Val<br>370 | Leu | Glu | Gly | Ala | Ile<br>375 | Asn | Phe | Gln | Arg | Asp<br>380 | Ala | Phe | Leu | Arg |
| Ile<br>385 | Asp | Met | Tyr | Ala | Met<br>390 | Gly | Leu | Val | Leu | Trp<br>395 | Glu | Leu | Val | Ser | Arg<br>400 |
| Cys | Lys | Ala | Ala | Asp<br>405 | Gly | Pro | Val | Asp | Glu<br>410 | Tyr | Met | Leu | Pro | Phe<br>415 | Glu |
| Glu | Glu | Ile | Gly<br>420 | Gln | His | Pro | Ser | Leu<br>425 | Glu | Glu | Leu | Gln | Glu<br>430 | Val | Val |
| Val | His | Lys<br>435 | Lys | Met | Arg | Pro | Thr<br>440 | Ile | Lys | Asp | His | Trp<br>445 | Leu | Lys | His |
| Pro | Gly<br>450 | Leu | Ala | Gln | Leu | Cys<br>455 | Val | Thr | Ile | Glu | Glu<br>460 | Cys | Trp | Asp | His |
| Asp<br>465 | Ala | Glu | Ala | Arg | Leu<br>470 | Ser | Ala | Gly | Cys | Val<br>475 | Glu | Glu | Arg | Val | Ser<br>480 |
| Leu | Ile | Arg | Arg | Ser<br>485 | Val | Asn | Gly | Ser | Thr<br>490 | Ser | Asp | Cys | Leu | Val<br>495 | Ser |
| Leu | Val | Thr | Ser<br>500 | Ser | Thr | Asn | Val | Asp<br>505 | Leu | Leu | Pro | Lys | Glu<br>510 | Ser | Ser |
| Ile |     |     |     |     |     |     |     |     |     |     |     |     |     |     |     |

( 2 ) INFORMATION FOR SEQ ID NO:12:

( i ) SEQUENCE CHARACTERISTICS:
        ( A ) LENGTH: 536 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..536
        ( D ) OTHER INFORMATION: /note= "HUMAN ACTIVIN TYPE II
              RECEPTOR"

( x i ) SEQUENCE DESCRIPTION: SEQ ID NO:12:

|     |     |     |     |     |     |     |     |     |     |     |     |     |     |     |
| --- | --- | --- | --- | --- | --- | --- | --- | --- | --- | --- | --- | --- | --- | --- |
| Met<br>1 | Thr | Ala | Pro | Trp<br>5 | Ala | Ala | Leu | Ala | Leu<br>10 | Leu | Trp | Gly | Ser | Leu<br>15 | Cys |
| Ala | Gly | Ser | Gly<br>20 | Arg | Gly | Glu | Ala | Glu<br>25 | Thr | Arg | Glu | Cys | Ile<br>30 | Tyr | Tyr |
| Asn | Ala | Asn<br>35 | Trp | Glu | Leu | Glu | Arg<br>40 | Thr | Asn | Gln | Ser | Gly<br>45 | Leu | Glu | Arg |
| Cys | Glu<br>50 | Gly | Glu | Gln | Asp | Lys<br>55 | Arg | Leu | His | Cys | Tyr<br>60 | Ala | Ser | Trp | Ala |
| Asn<br>65 | Ser | Ser | Gly | Thr | Ile<br>70 | Glu | Leu | Val | Lys | Lys<br>75 | Gly | Cys | Trp | Leu | Asp<br>80 |
| Asp | Phe | Asn | Cys | Tyr<br>85 | Asp | Arg | Gln | Glu | Cys<br>90 | Val | Ala | Thr | Glu | Glu<br>95 | Asn |
| Pro | Gln | Val | Tyr<br>100 | Phe | Cys | Cys | Cys | Glu<br>105 | Gly | Asn | Phe | Cys | Asn<br>110 | Glu | Arg |
| Phe | Thr | His<br>115 | Leu | Pro | Glu | Pro | Gly<br>120 | Gly | Pro | Glu | Val | Thr<br>125 | Tyr | Glu | Pro |
| Pro | Pro<br>130 | Thr | Ala | Pro | Thr | Leu<br>135 | Leu | Thr | Val | Leu | Ala<br>140 | Tyr | Ser | Leu | Leu |

```
Pro  Ile  Gly  Gly  Leu  Ser  Leu  Ile  Val  Leu  Leu  Ala  Phe  Trp  Met  Tyr
145                      150                      155                      160

Arg  His  Arg  Lys  Pro  Pro  Tyr  Gly  His  Val  Asp  Ile  His  Glu  Val  Arg
                    165                      170                      175

Gln  Cys  Gln  Arg  Trp  Ala  Gly  Arg  Arg  Asp  Gly  Cys  Ala  Asp  Ser  Phe
                    180                      185                      190

Lys  Pro  Leu  Pro  Phe  Gln  Asp  Pro  Gly  Pro  Pro  Pro  Ser  Pro  Leu
               195                      200                      205

Val  Gly  Leu  Lys  Pro  Leu  Gln  Leu  Leu  Glu  Ile  Lys  Ala  Arg  Gly  Arg
     210                      215                      220

Phe  Gly  Cys  Val  Trp  Lys  Ala  Gln  Leu  Met  Asn  Asp  Phe  Val  Ala  Val
225                      230                      235                      240

Lys  Ile  Phe  Pro  Leu  Gln  Asp  Lys  Gln  Ser  Trp  Gln  Ser  Glu  Arg  Glu
               245                      250                      255

Ile  Phe  Ser  Thr  Pro  Gly  Met  Lys  His  Glu  Asn  Leu  Leu  Gln  Phe  Ile
               260                      265                      270

Ala  Ala  Glu  Lys  Arg  Gly  Ser  Asn  Leu  Glu  Val  Glu  Leu  Trp  Leu  Ile
          275                      280                      285

Thr  Ala  Phe  His  Asp  Lys  Gly  Ser  Leu  Thr  Asp  Tyr  Leu  Lys  Gly  Asn
     290                      295                      300

Ile  Ile  Thr  Trp  Asn  Glu  Leu  Cys  His  Val  Ala  Glu  Thr  Met  Ser  Arg
305                      310                      315                      320

Gly  Leu  Ser  Tyr  Leu  His  Glu  Asp  Val  Pro  Trp  Cys  Arg  Gly  Glu  Gly
                    325                      330                      335

His  Lys  Pro  Ser  Ile  Ala  His  Arg  Asp  Phe  Lys  Ser  Lys  Asn  Val  Leu
               340                      345                      350

Leu  Lys  Ser  Asp  Leu  Thr  Ala  Val  Leu  Ala  Asp  Phe  Gly  Leu  Ala  Val
          355                      360                      365

Arg  Phe  Glu  Pro  Gly  Lys  Pro  Pro  Gly  Asp  Thr  His  Gly  Gln  Val  Gly
     370                      375                      380

Thr  Arg  Arg  Tyr  Met  Ala  Pro  Glu  Val  Leu  Glu  Gly  Ala  Ile  Asn  Phe
385                      390                      395                      400

Gln  Arg  Asp  Ala  Phe  Leu  Arg  Ile  Asp  Met  Tyr  Ala  Met  Gly  Leu  Val
               405                      410                      415

Leu  Trp  Glu  Leu  Val  Ser  Arg  Cys  Lys  Ala  Ala  Asp  Gly  Pro  Val  Asp
               420                      425                      430

Glu  Tyr  Met  Leu  Pro  Phe  Glu  Glu  Ile  Gly  Gln  His  Pro  Ser  Leu
          435                      440                      445

Glu  Glu  Leu  Gln  Glu  Val  Val  Val  His  Lys  Lys  Met  Arg  Pro  Thr  Ile
     450                      455                      460

Lys  Asp  His  Trp  Leu  Lys  His  Pro  Gly  Leu  Ala  Gln  Leu  Cys  Val  Thr
465                      470                      475                      480

Ile  Glu  Glu  Cys  Trp  Asp  His  Asp  Ala  Glu  Ala  Arg  Leu  Ser  Ala  Gly
               485                      490                      495

Cys  Val  Glu  Glu  Arg  Val  Ser  Leu  Ile  Arg  Arg  Ser  Val  Asn  Gly  Thr
               500                      505                      510

Thr  Ser  Asp  Cys  Leu  Val  Ser  Leu  Val  Thr  Ser  Val  Thr  Asn  Val  Asp
          515                      520                      525

Leu  Leu  Pro  Lys  Glu  Ser  Ser  Ile
530                      535
```

MORPHOGEN CELL SURFACE RECEPTOR

This is a divisional of copending application(s) Ser. No. 08/357,533 filed on Dec. 16, 1994 which is a continuation of U.S. Ser. No. 08/073,199, filed Jun. 7, 1993 now abandoned.

FIELD OF THE INVENTION

This invention relates generally to the field of tissue morphogenesis and more particularly to novel sequences encoding morphogen cell surface receptors.

BACKGROUND OF THE INVENTION

Cell differentiation is the central characteristic of tissue morphogenesis which initiates during embryogenesis, and continues to various degrees throughout the life of an organism in adult tissue repair and regeneration mechanisms. The degree of morphogenesis in adult tissue varies among different tissues and is related, among other things, to the degree of cell turnover in a given tissue.

The cellular and molecular events which govern the stimulus for differentiation of cells is an area of intensive research. In the medical and veterinary fields, it is anticipated that the discovery of the factor or factors which control cell differentiation and tissue morphogenesis will advance significantly medicine's ability to repair and regenerate diseased or damaged mammalian tissues and organs. Particularly useful areas for human and veterinary therapeutics include reconstructive surgery and in the treatment of tissue degenerative diseases including arthritis, emphysema, osteoporosis, cardiomyopathy, cirrhosis, degenerative nerve diseases, inflammatory diseases, and cancer, and in the regeneration of tissues, organs and limbs. In non-mammalian systems, such as insect systems, the discovery of such factors provide the basis for developing potent insecticides by, for example, identifying compounds which inhibit or otherwise interfere with the morphogenetic effect of these factors in the insect. (In this and related applications, the terms "morphogenetic" and "morphogenic" are used interchangeably.)

A number of different factors have been isolated in recent years which appear to play a role in cell differentiation. Recently, various members of the structurally related proteins of the transforming growth factor-β (TGF-β) superfamily of proteins have been identified as true tissue morphogens.

This "family" of proteins, constituting a distinct subfamily within the TGF-β superfamily of structurally related proteins, share substantial amino acid sequence homology within their morphogenically active C-terminal domains, including a conserved six or seven cysteine skeleton, and are capable of inducing tissue-specific morphogenesis in a variety of organs and tissues. The proteins apparently contact and interact with progenitor cells e.g., by binding suitable cell surface molecules, predisposing or otherwise stimulating the cells to proliferate and differentiate in a morphogenically permissive environment. The morphogens are capable of inducing the developmental cascade of cellular and molecular events that culminate in the formation of new organ-specific tissue, including any vascularization, connective tissue formation, and nerve innervation as required by the naturally occurring tissue.

A number of proteins useful in tissue morphogenesis have been identified to date, including proteins originally identified as bone inductive proteins, such as the OP-1, (also referred to in related applications as "OP1"), OP-2 (also referred to in related applications as "OP2"), OP-3 and the CBMP2 proteins, as well as amino acid sequence-related proteins such as BMP5, BMP6 and its murine homolog, Vgr-1, dpp and 60A (from Drosophila), Vgl (from Xenopus), and GDF-1 (from mouse.) See, for example, PCT documents US92/01968 and US92/07358 (published as WO 92/15323 and WO 93/04692, respectively), the disclosures of which are incorporated herein by reference. These TGF-β superfamily members comprise a distinct subfamily of proteins different from other members of the TGF-β superfamily in that the family of morphogenic proteins are able to induce the full cascade of events that result in formation of functional tissue rather than merely inducing formation of fibrotic (scar) tissue as, for example, TGF-β does in many cases. Specifically, members of the morphogen family of proteins are capable of all of the following in a morphogenically permissive environment: stimulating cell proliferation and cell differentiation, and supporting the growth and maintenance of differentiated cells. The morphogenic proteins apparently may act as endocrine, paracrine or autocrine factors.

These proteins are capable of significant species "crosstalk." For example, dpp and 60A, two Drosophila proteins, can induce endochondral bone formation at a non-bony site in a standard rat bone formation assay. In their native form, however, the proteins appear to be tissue-specific, each protein expressed in or provided to one or only a few tissues or, alternatively, expressed only at particular times during development. For example, OP-1 is expressed and/or present primarily in tissues of urogenital origin or bone tissue, although it has been identified in mammary, salivary gland tissue, and reproductive tissues, as well as in gastrointestinal tract tissue. GDF-1 appears to be expressed primarily in neural tissue, while OP-2 appears to be expressed in early (e.g., 8-day) mouse embryo. The endogenous morphogens may be synthesized by the cells on which they act, by neighboring cells, or by cells of a distant tissue, the secreted protein being transported to the cells to be acted on.

Recently, the genetic sequences encoding receptors to several members of the TGF-β protein superfamily have been described. Lin et al. (1992) *Cell* 68:775–785, disclose the expression cloning of the TGF-β Type II receptor. Several groups have described genetic sequences encoding various activin (Type II) receptors in different species, including mouse, rat, xenopus, and human. The overall amino acid sequence homology between these activin receptors is 50–80%. See, Matthews et al. (1991) *Cell* 65:973–982 and international patent application WO 92/20793, published Nov. 26, 1992, disclosing the "ActR II" sequence; Attisano et al., (1992) Cell 68:97–108, disclosing the "ActR-IIB" sequence; and Legerski et al. (1992) *Biochem Biophys. Res.Comm'n* 183:672–679. By amino acid sequence homology to the TGF-β and activin Type II receptor sequences, the daf-1 gene, (Georgi et al. (1990) *Cell* 61:635–645), identified in *C. elegans* and having no known ligand to date, also is believed to encode a receptor for a TGF-β superfamily protein member. These disclosed receptors for TGF-β and activin are distinct from cell surface receptors capable of specific binding interaction with the morphogens described herein, and do not bind these morphogens significantly (see, for example, Legerskie et al. (1992) *Biochem. Biophys.Res. Comm'n*. 183:672–679 and Attisano et al., (1992) *Cell* 68:97–108.)

To date, the molecule or molecules with which the morphogens described herein interact on the cell surface have not yet been identified. Identification of these cell surface molecules, with which the morphogens interact and through which they may mediate their biological effect, is anticipated to significantly enhance elucidation of the molecular mechanism of tissue morphogenesis and to enable development of morphogen receptor binding "analogs", e.g., compounds (which may or may not be amino acid-based macromolecules) capable of mimicking the binding affinity of a morphogen for its receptor sufficiently to act either as a receptor binding agonist or antagonist. These "analogs" have particular utility in therapeutic, diagnostic and experimental research applications.

It is an object of this invention to provide nucleic acid and amino acid sequences encoding a morphogen binding cell surface receptor, including allelic, species, chimeric and mutant variants thereof. Another object is to provide methods for identifying genes in a variety of species and/or tissues, and in a variety of nucleic acid libraries encoding morphogen receptors which share little or no substantial amino acid identity with the extracellular domains of known TGF-β or activin receptor molecules. Still another object is to provide means for the expression of morphogen receptors, including truncated forms thereof, using recombinant DNA technology. Yet another object is to provide means for designing biosynthetic morphogen receptor-binding ligands and/or for identifying natural-occurring ligands, including morphogen agonists and antagonists, using the morphogen receptor molecules of this invention, and analogs thereof. Still another object is to provides means and compositions for modulating the endogenous expression or concentration of these receptor molecules. Yet another object is to provide compositions and methods for creating useful insecticides. These and other objects and features of the invention will be apparent from the description, drawings and claims which follow.

SUMMARY OF THE INVENTION

A novel genetic sequence encoding a novel polypeptide chain, referred to herein as MR-1 (morphogen receptor-1) now has been discovered. Accordingly, the invention provides novel, substantially pure nucleic acid and amino acid sequences encoding the morphogen receptor, means for producing morphogen receptor polypeptide chains using recombinant DNA technology, means for identifying sequences encoding other morphogen receptors ("MR"), and means for designing morphogen receptor binding analogs, referred to herein as morphogen analogs.

The morphogen receptors of this invention share a conserved structure, including an extracellular domain generally composed of about 120–150 amino acids, a transmembrane domain sufficient to span a cellular membrane one time, and an intracellular (cytoplasmic) domain having serine/threonine kinase activity. The morphogen receptors of this invention share little or no substantial amino acid sequence identity (e.g., less than 30%) with the extracellular ligand binding domains of known Type II TGF-β or activin receptor molecules. In a preferred aspect of the invention, morphogen receptors share less than 26% amino acid sequence identity with the extracellular ligand binding domains of known TGF-β or activin receptor molecules.

As used herein, "morphogen analog" refers to any molecule capable of mimicking the binding activity of a morphogen sufficiently to act as a morphogen receptor binding ligand. These analog ligands may act as morphogen agonists capable of mimicking the morphogen both in receptor binding and in inducing a transmembrane effect. Alternatively, the analog ligands may act as morphogen antagonists, capable of mimicking the morphogen in receptor binding, thereby blocking the natural morphogen from interacting with its receptor, but without inducing a transmembrane effect, for example. Morphogen analogs may be amino acid-based, or may be composed of other chemical structures, and may be naturally sourced or synthetically produced.

As used herein, "amino acid sequence homology" is understood to mean amino acid sequence similarity, and homologous sequences share identical or similar amino acids, where similar amino acids are conserved amino acids as defined by Dayoff et al., *Atlas of Protein Sequence and Structure*; vol.5, Suppl.3, pp.345–362 (M. O. Dayoff, ed., Nat'l BioMed. Research Fdn., Washington D.C. 1978.) Thus, a candidate sequence sharing 60% amino acid homology with a reference sequence requires that, following alignment of the candidate sequence with the reference sequence, 60% of the amino acids in the candidate sequence are identical to the corresponding amino acid in the reference sequence, or constitute a conserved amino acid change thereto. "Amino acid sequence identity" is understood to require identical amino acids between two aligned sequences. Thus, a candidate sequence sharing 60% amino acid identity with a reference sequence requires that, following alignment of the candidate sequence with the reference sequence, 60% of the amino acids in the candidate sequence are identical to the corresponding amino acid in the reference sequence.

As used herein, all homologies and identities calculated use MR-1 as the reference sequence, with the extracellular domain reference sequence constituting residues 25–147 of Seq. ID No. 1; and the intracellular domain reference sequence constituting residues 209–492 of Seq. ID No. 1. Also as used herein, sequences are aligned for homology and identity calculations as follows: Sequences are aligned by eye to maximize sequence identity. Where amino acid extracellular domain sequences are compared, the alignment first maximizes alignment of the cysteines present in the two sequences, then modifies the alignment as necessary to maximize amino acid identity and similarity between the two sequences. Where amino acid intracellular domain sequences are compared, sequences are aligned to maximize alignment of conserved amino acids in the kinase domain, where conserved amino acids are those identified by boxes in FIG. 3. The alignment then is modified as necessary to maximize amino acid identity and similarity. In all cases, internal gaps and amino acid insertions in the candidate sequence as aligned are ignored when making the homology/identity calculation. Exemplary alignments are illustrated in FIGS. 2 and 3 where the amino acid sequences for the extracellular and intracellular domains, respectively are presented in single letter format. In the figures "gaps" created by sequence alignment are indicated by dashes. See, for example, in FIG. 3, the four dashes occurring after "CEHF" at position 39 in the MR-1 sequence. Of course, the next amino acid in the MR-1 sequence is "D", aspartic acid, which appears following the dashes, at position 40.

Also as used herein, "mutant variant" is understood to mean an amino acid variant form of the receptor molecule wherein the amino acid changes in the sequences do not alter significantly the activity (e.g., morphogen binding or kinase activity) of the receptor molecule, and the variant molecule performs substantially the same function in substantially the same way as the naturally occurring form of the molecule. These variants also may be naturally occurring or may be biosynthetically constructed by using standard recombinant DNA techniques or chemical protein synthesis methodologies. In a preferred embodiment, these mutant variants having a binding affinity for a morphogen ligand with a Kd less than about $10^{-7}$M (see below.)

Finally, as used herein, ligand-receptor binding specificity is understood to mean a specific, saturable noncovalent interaction between the ligand and the receptor, and which is subject to competitive inhibition by a suitable competitor molecule. Preferred binding affinities (defined as the amount of ligand required to fill one-half (50%) of available receptor binding sites) are described herein by dissociation constant (Kd). Preferred binding affinities of ligands having specificity for a given receptor molecule of the invention have a Kd of less than $10^{-7}$M, preferably less than $10^{-8}$M. In another preferred embodiment, the receptor molecules have little or no substantial binding affinity for TGF-β or activin. That is, TGF-β and activin (or inhibin) have a binding affinity for the morphogen receptors of this invention with a Kd greater than $10^{-7}$M.

Useful morphogen receptor polypeptide chains include those encoded by the DNA sequence of SEQ ID NO. 1, including allelic and species variants thereof, as well as other naturally occurring and biosynthetic mutants, including truncated forms thereof.

In one aspect, the morphogen receptor polypeptide chains of this invention comprise: (1) an extracellular domain defining a three-dimensional conformation capable of binding a morphogen with specificity, (2) a transmembrane domain sufficient to span a cellular membrane, and (3) an intracellular (cytoplasmic) domain that is activated in response to the binding interaction of the extracellular domain with a morphogen or a morphogen analog.

In a preferred embodiment, the morphogen receptor comprises a polypeptide chain having a sequence of about 500 amino acids, glycosylated under naturally-occurring conditions, and comprising a molecular weight of about 58–90 kDa. As used herein, all molecular weights are apparent molecular weights, determined by comparison to molecular weight standards on a standard SDS-polyacrylamide electrophoresis gel.

In another embodiment, the morphogen receptor comprises an unglycosylated polypeptide chain having a sequence of at least about 120 amino acids and a molecular weight of about 15 kDa, or of about 500 amino acids and a molecular weight of about 59 kDa.

In another aspect, the polypeptide chains of this invention include truncated forms of the sequence of SEQ ID NO. 1, including allelic, species and mutant variants thereof, comprising the extracellular domain, or a portion thereof sufficient to bind a morphogen or morphogen analog with specificity. A currently preferred truncated form includes polypeptide chains comprising an amino acid sequence having less than about 200 amino acids and comprising part or all of the sequence defined by residues 25–147 of SEQ ID NO. 1.

In another aspect of the invention, the polypeptide chains of this invention include a truncated form of the sequence of ID NO. 1, including allelic, species and mutant variants thereof, comprising at least the cytoplasmic domain, and preferably part or all of the transmembrane domain as well. A currently preferred "intracellular" truncated form includes polypeptide chains comprising part or all of the sequences defined by residues 209–492 of Seq. ID No. 1, or residues 173–492 therein, or residues 148–492 therein.

In still another aspect of the invention, the polypeptide chains of this invention include a truncated form of the sequence of ID NO. 1, including allelic, species and mutant variants thereof, comprising at least the extracellular or cytoplasmic domain or a fragment thereof, linked to a peptide sequence useful for anchoring the polypeptide chain to a surface. Such anchors have particular utility for purification of the protein. A currently preferred anchor sequence particularly useful for purification protocols is a sequence comprising six histidines, referred to herein and in the art as a "hexa-His" or $(His)_6$ sequence. Another preferred anchor sequence useful for intracellular truncated forms includes peptide sequences, e.g., 5–15 amino acids in length, preferably derived from the C-terminal end of the extracellular domain.

In still another aspect of the invention, the polypeptide chains of this invention include chimeric receptor molecules comprising both an extracellular and intracellular (cytoplasmic) domain, and wherein at least either the extracellular domain or the cytoplasmic domain is encoded by the appropriate subpart of the sequence of SEQ ID NO. 1, including allelic, species and mutant variants thereof. In still another aspect, the extracellular or intracellular domains themselves may constitute chimeric sequences comprising the appropriate subpart of the sequence of Seq. ID NO. 1.

In another aspect, the invention comprises receptor molecules having an extracellular ligand binding domain having less than 30% amino acid identity, and preferably less than 20% amino acid identity with the ligand binding domain of activin Type II receptors, or TGF-β Type II receptors currently known in the art.

In another aspect, the invention comprises morphogen receptor molecules capable of specific binding interaction with a morphogen. In one preferred embodiment, the morphogen comprises the amino acid sequence of the drosophila proteins DPP or 60A. In another preferred embodiment, the morphogen comprises OP-1 or species, allelic and mutant variants thereof. In another preferred embodiment the morphogen comprises the amino acid sequence of OP-2 or OP-3, Vgr-1, Vgl, BMP2-6, GDF-1, or Generic Sequences 1–6, defined in PCT US92/01968, published as WO 92/15323.

Another aspect of the invention comprises morphogen receptor polypeptide chains capable of binding a morphogen with specificity, having little or no substantial amino acid identity with the extracellular domain of known TGF-β or activin receptors, and encoded by nucleic acid which hybridize to part or all of the cytoplasmic domain of MR-1 (residues 209–492) of SEQ ID NO. 1 under low stringent hybridization conditions. As used herein, low stringency hybridization conditions are understood to be those defined in Maniatis et al. *Molecular Cloning (A laboratory Manual)*, Cold Spring Harbor Laboratory 2nd Ed. (1989). Exemplary conditions include: hybridization in 30% formamide, 5×SSPE, 5×Denhardt's Solution, and 0.5% SDS at 37° C. overnight, and washing in 2.0×SSPE, 0.5% SDS at 37° C.

In another aspect, the encoding nucleic acids hybridize with a nucleic acid that encodes either the extracellular domain or the intracellular domain under high stringency conditions, as defined in Maniatis et al.

In still another aspect, the invention comprises morphogen receptor polypeptide chains capable of binding a morphogen or morphogen analog with specificity and encoded by nucleic acids which hybridize with a nucleic acid that encodes part or all of the extracellular domain of Seq. ID No. 1 under low stringency conditions.

In another aspect, the invention comprises morphogen receptor molecules capable of binding a morphogen with specificity but having little binding affinity for TGF-β or activin, and encoded by nucleic acids that can be amplified with any of the primer sequences described below (SEQ ID NOS. 4–7, respectively) in a standard PCR amplification protocol:

PRIMER #1: ATTSKWRCTY TTGADGTCSC KGTG
(Seq. ID NO. 4)
PRIMER #2: ATYGCBCACM GSGAYHTCAA RAG
(Seq. ID NO. 5)
PRIMER #3: GAATCTGTSG CHGTSAARRT HTTYCC
(Seq. ID NO. 6)
PRIMER #4: TCCAGSACYT CNGGDGCCAK RTA
(Seq. ID NO. 7).

In one preferred embodiment, the primers are modified to reflect a non-drosophila codon bias, preferably a human codon bias.

In another aspect, the invention provides a method for identifying genetic sequences encoding human and other mammalian morphogen receptors by first identifying sequences encoding these receptors in a drosophila or other genome having less complexity than a mammalian genome and likely to encode fewer members of the family of morphogen receptors, and using the thus identified receptor sequences to locate their mammalian homologs. Because of the significant species "cross talk" evidenced by morphogens (e.g., ability of these proteins to be biologically active across different species, including forming the necessary interactions with xenogenic morphogen receptors) it is anticipated that this approach to locating mammalian receptor sequences will be reliable and ease identification of the genes encoding this family of receptors in mammals.

In another preferred embodiment, the morphogen receptor molecules have less than 30% amino acid identity, preferably less than 26% identity, in their extracellular domains with the extracellular domain of activin A or activin B Type II receptors, or TGF-β Type II receptors.

In another aspect, the invention comprises molecules capable of binding a morphogen with specificity and sharing at least 30% amino acid sequence identity with the sequence defined by residues 25–147 of Seq. ID No. 1, preferably at least 40%, more preferably 50%, identity. In another aspect, the invention comprises receptor molecules comprising both an extracellular and intracellular domain, wherein the amino acid sequence of the receptor molecule shares at least 35% amino acid sequence identity, preferably at least 55%, and more preferably at least 65% identity with the sequence defined by residues 210–490 of Seq. ID No. 1, and wherein the receptors have little or no binding affinity for activin or TGF-β (e.g., binding affinity of these receptors for these ligands have a Kd greater than $10^{-7}$M.)

In still another aspect, the invention provides molecules useful in the design and/or identification of morphogen analogs as described below. The molecules useful in these assays may include part or all of the sequence of SEQ ID NO. 1, including allelic, species and mutant variants thereof. Currently preferred for these assays are molecules comprising at least the sequence which defines the extracellular domain, e.g., residues 25–147. The morphogen analogs identified in these assays may act as morphogen agonists or antagonists.

In one embodiment of the invention, useful morphogen analogs include antibodies capable of specifically recognizing and binding to the morphogen binding surface of the receptor. These antibodies may be monoclonal or polyclonal, or may be biosynthetic derivatives thereof, including, but not limited to, for example, monoclonal fragments, such as single chain $F_v$ fragments, referred to in the literature as $sF_v$s, BABs and SCAs, and chimeric monoclonals, in which portions of the monoclonals are humanized (excluding those portions involved in antigen recognition (e.g., complementarity determining regions, "CDRs".) See, for example, U.S. Pat. No. 5,091,513, 5,132, 405, and U.S. Ser. No. 955,399, soon to issue as U.S. Pat. No. 5,258,498 Biosynthetic chimeras, fragments and other antibody derivatives may be synthesized using standard recombinant DNA methodology and/or automated chemical nucleic acid synthesis methodology well described in the art and as described below.

In another embodiment of the invention, antibodies to the intracellular domain are contemplated. These antibodies will have particular utility in receptor purification schemes.

In still another aspect the invention comprises molecules useful in screening assays to identify molecules that modulate endogenous morphogen receptor concentrations. Useful assay methodologies may be modeled on those described in PCT US92/07359 (published as WO 93/05172), and as described below.

In another embodiment, useful antagonists include soluble forms of the receptor binding surface which are capable of competing for morphogen binding at a target site. Useful applications for antagonists include their use as therapeutics to modulate uncontrolled differentiated tissue growth, such as malignant transformations as occurs, for example, in osteosarcomas or Paget's disease. Still other useful applications include their use as insecticides, where the antagonist is a molecule having specificity for a non-mammalian insect-specific morphogen receptor and can inhibit or otherwise interfere with insect growth and tissue development.

The invention thus relates to compositions and methods for the use of morphogen receptor polypeptide chains in diagnostic, therapeutic and experimental procedures. Active morphogen receptors useful in the compositions and methods of this invention may include truncated or full length forms, as well as forms having varying glycosylation patterns. Active morphogen receptors of the invention also include chimeric constructs as described below, comprising both an MR-1 sequence and a non-MR-1 sequence. Active MR-1 can be expressed from intact or truncated genomic or cDNA, or from synthetic DNAs in procaryotic or eucaryotic host cells, and purified, cleaved, refolded and oxidized as necessary to form active molecules. Useful host cells include prokaryotes, including *E. coli* and *B. subtilis*, and eukaryotic cells, including mammalian cells, such as fibroblast 3T3 cells, CHO, COS, melanoma or BSC cells, Hela and other human cells, the insect/baculovirus system, as well as yeast and other microbial host cell systems.

Thus, in view of this disclosure, skilled genetic engineers can isolate genes from libraries of various different species which encode appropriate amino acid sequences, or construct them from oligonucleotides, and can express these genetic sequences in various types of host cells to produce large quantities of morphogen receptor polypeptide chains capable of binding morphogens.

BRIEF DESCRIPTION OF THE DRAWINGS

FIG. 2 is a homology alignment of the extracellular domains of MR-1 and other known receptors which bind various members of the TGF-β superfamily of structurally related proteins, aligned to maximize amino acid identity, and wherein conserved amino acids are identified by boxes; and FIG. 3 is a homology alignment of the intracellular domain of MR-1 and the various known receptors for proteins in the TGF-β superfamily of structurally related proteins, aligned to maximize amino acid identity, and wherein conserved amino acids are boxed. Asterisks indicate the regions of high amino acid and/or nucleotide sequence homology on which PCR primer sequences were based.

DETAILED DESCRIPTION

Figure 1:
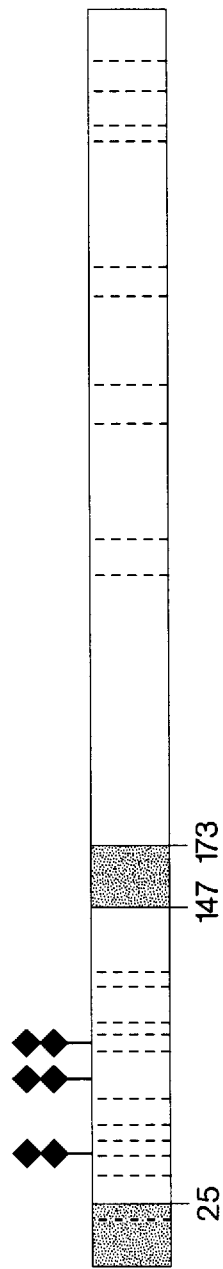
FIG. 1 is a schematic representation of the encoded MR-1 amino acid sequence, wherein the first and second stippled regions identify the signal sequence and transmembrane domains, respectively; the first open box identifies the extracellular binding ligand binding domain; the second open box identifies the intracellular serine/threonine kinase domain; broken lines indicate the position of cysteine residues; diamonds indicate potential glycosylation sites, and the numbers appearing below the sequence indicate amino acid residues.

A cloning protocol has been developed which enables identification of nucleic acid sequences encoding a morphogen cell surface receptor (MR-1). The protocol takes advantage of the significant "cross talk" among morphogen species variants, and relies on a PCR DNA amplification procedure as disclosed herein for identifying genetic sequences in a Drosophila genome and encoding candidate receptor molecules. DNAs encoding candidate morphogen receptor molecules are DNAs encoding membrane spanning molecules having extracellular domains sharing less than 30% identity and preferably less than 26% identity with the extracellular domains of other, known receptor molecules whose ligands are members of the TGF-β superfamily (e.g., the daf-1 receptor and the Type II TGF-β and activin receptors.) The thus identified sequences found to encode morphogen receptors then can be used to identify their mammalian, including human, homologs and related variants.

The Drosophila genome was chosen herein as the source genome as an example of a genetically less complex genome likely to encode fewer members of the family of morphogen receptors identified to date in mammals. Other genomes, such as that of Xenopus, for example, also may be used to advantage. Because of the significant species "cross talk" evidenced by morphogens (e.g., ability of these proteins to be biologically active across different species, including forming the necessary interactions with xenogenic morphogen receptors) it is anticipated that this approach to locating mammalian receptor sequences will be reliable and ease identification of the genes encoding this family of receptors.

The cloning protocol allows identification and recombinant expression of a novel protein, MR-1, comprising an extracellular domain, a transmembrane region and a cytoplasmic domain, and which is capable of binding one or more morphogens with specificity. The protein has been characterized as follows: its nucleotide and encoded amino acid sequences have been determined, its potential glycosylation sites have been identified in the amino acid sequence, antibodies to the protein have been raised and tested, and portions of the protein have been recombinantly produced.

Identification of MR-1, including identification of its nucleic acid sequence, allows creation of probes to identify other morphogen receptor (MR) sequences in other species, as well as to detect the tissue distribution of MR expression. The probes may be derived from MR-1, preferably derived from the extracellular domain, and modified, for example, to account for a preferred species codon bias. Alternatively, the MR-1 sequence information may be used to refine the primer sequences described below, or to design other degenerate primer sequences for amplifying other DNAs. Under naturally occurring conditions, individual morphogens are preferentially expressed in, or preferentially act on, different tissues. Accordingly, it is anticipated that a family of morphogen receptors exist that are expressed preferentially in different tissues and which bind preferentially with preferred members of the morphogen family of proteins.

The morphogen receptor disclosed herein, MR-1, including allelic, species and mutant variants of MR-1, also can be used in protocols to identify receptor binding ligands that function as morphogen analogs and which may be used as morphogen agonists or antagonists, for therapeutic, diagnostic and experimental uses as described herein below. These ligands may be naturally occurring molecules identified in, for example, a high flux screen, or they may be designed and biosynthetically created using a rational drug design and established structure/function analysis. The ligands may be amino acid-based or may be composed of non-proteinaceous chemical structures. Useful ligands also may be antibodies, preferably monoclonal antibodies or synthetic derivatives thereof, such as monoclonal single chain $F_v$ fragments known in the art as $sF_vs$, BABs, and SCAs (see below.) Moreover, soluble forms of the protein, e.g., forms consisting essentially of the extracellular domain or a fragment thereof sufficient to bind a morphogen with specificity, may be used as a soluble therapeutic morphogen antagonists, as described below.

The MR sequence identified herein also may be used to create chimeric MR sequences, wherein, for example, part or all of either the extracellular domain or the intracellular domain is a non-MR sequence or is a sequence from another, non-MR-1 morphogen receptor sequence. These chimeric MR polypeptide chains may be synthesized using standard recombinant DNA methodology and/or automated chemical nucleic acid synthesis methodology well described in the art and as disclosed below. Chimerics may be useful, for example, in morphogen analog assays, wherein the MR extracellular binding domain is coupled to an intracellular domain that is well characterized and/or readily detectable as a second messenger response system, as described below.

The cloning procedure for obtaining MR nucleic acid sequences, as well as other material aspects concerning the nature and utility of these sequences, including how to make and how to use the subject matter claimed, will be further understood from the following, which constitutes the best mode currently contemplated for practicing the invention.

EXAMPLE 1

Identification of MR-1

A. Cloning

A morphogen receptor gene sequence was isolated by PCR amplification, using degenerate sequences as primers to amplify a DNA fragment of Drosophila genomic DNA. The Drosophila genome, known to encode at least two morphogens, dpp and 60A, was chosen as the initial probing library because of its smaller size compared to that of higher organisms. The PCR primer sequences were designed based on predictions from observed homologies with the deduced amino acid sequences of known receptor sequences of other members of the TGF-β superfamily of proteins, using a Drosophila codon bias and creating degeneracies within the sequence as necessary.

Specifically, genetic sequences encoding TGF-β Type II and activin Type II receptor molecules are known, as is the daf-1 receptor from *C. elegans* (see Lin et al., (1992) *Cell* 68:775–785; Matthews et al, (1991) *Cell* 65:973–982; Attisano et al., (1992) *Cell* 68:97–108; and Georgi et al., (1990) *Cell* 61:635–645, respectively, and in Seq. ID Nos. 8–11, respectively.) All four receptors share the same overall structure, having a relatively short extracellular domain, a transmembrane sequence sufficient to span the cellular membrane once, and an intracellular sequence that is believe to act as a serine/threonine kinase. While the extracellular domains of the TGF-β, activin and daf-1 receptors share little amino acid homology or identity, the intracellular domains share more homology (between about 30–65% amino acid identity.) The various activin receptor species share between about 55–78% amino acid identity in their extracellular and intracellular domains.

TGF-β and activin, known ligands for two of the three receptors, also share a similar overall structural motif with each other and with morphogens, based on a conserved cysteine pattern within their C-terminal domains. Several of the morphogenic activities characteristic of morphogens also are demonstrated by TGF-β and activin/inhibins. Accordingly, on the belief that the morphogen receptors also likely share a similar overall structural motif with the Type II TGF-β and activin receptors, the intracellular serine/threonine kinase domains of the known receptors were aligned and regions of high amino acid homology identified for designing degenerate primer sequences. Four candidate regions were identified, indicated by asterisks in FIG. 3. The number in parentheses beneath these asterisks corresponds to the primer number.

Oligonucleotides were prepared with degeneracies (512 fold) introduced to include multiple probable sequences encoding this amino acid sequence, while maintaining the preferred Drosophila codon bias. In addition, where possible, observed conserved nucleotide sequences were exploited. The four primers created (#1–4) are shown below:

Primer 1 (#3501): ATT SKW RCT YTT GAD GTC SCK GTG SEQ ID NO: 4

Primer 2 (#3502): ATY GCB CAC MGS GAY HTC AAR AG SEQ ID NO: 5

Primer 3 (#3503): GAA TCT GTS GCH GTS AAR RTH TTY CC SEQ ID NO: 6

Primer 4 (#3504): TCC AGS ACY TCN GGD GCC AKR TA SEQ ID NO: 7

Single Letter Code (IUPAC):
R=A or G Y=C or T M=A or C K=G or T S=C or G W=A or T H=A or C or T B=C or G or T V=A or C or G D=A or G or T N=A or C or G or T These primers then were used in a PCR reaction using Drosophila genomic DNA and standard procedures well known in the art, see for example, Saiki et al. (1985) *Science* 230:1350–1354.

Briefly, degenerate oligonucleotides were synthesized on a standard automated DNA synthesizer, (e.g., Cruachem PS250, Scotland) following manufacturer's instructions, and then purified using standard procedures.

PCR reactions were performed with a commercially available thermal cycler and reagent kit (e.g., GeneAmp, Perkins & Elmer Corp., Norwalk) and following the manufacturer's instructions in a standard PCR protocol: in a 100 μl final volume with 1 μg drosophila genomic DNA, 1 μM final concentration of each primer, 0.2 mM dNTP's, 50 mM KCl 10 mM Tris-HCl(pH 9.0 at 25° C.) 0.1% Triton X-100, 1.5 mM MgCl$_2$, 2.5 units of Taq polymerase. The reaction mixture was heated to 60° C. before addition of the nucleotides and polymerase and amplification was performed for 40 cycles:

| program: | 94° C. 1 min |
| | 55° C. 1 min. 30 sec. |
| | 72° C. 1 min. 20 sec. + 1 sec followed by a single extension of |
| | 72° C. 5 min. |
| | 4° C. hold |

Amplified products then were separated by standard polyacrylamide gel electrophoresis, and fragments of the appropriate size (e.g., 474 bases) excised and purified using standard procedures. These fragments then were subcloned into a standard, commercially available cloning vector (e.g., available from Invitrogen Inc., San Diego) compatible with the PCR-generated DNA fragment ends. DNA from individual clones then was prepared by standard alkaline lysis and the isolated DNAs sequenced using standard procedures and commercially available reagents (e.g., dideoxy sequencing, U.S. BioChem Sequencing Kit, Cleveland.)

PCR amplification with primers 3 and 4 identified a 470 base pair fragment, a partial sequence of which appears in Seq. ID No. 3, and corresponding to the nucleotide sequence encoding residues 224 to 382 of Seq. ID No. 1. The 470 base pair fragment then was used to create a probe sequence (by random priming) for standard DNA library screening under high stringency conditions (e.g., washed at 0.1×SSPE, 0.1% SDS, at 50 C) to identify the complete coding sequence in a Drosophila cDNA library (UniZAPXR Drosophila embryo cDNA library, Stratagene, La Jolla) and standard library screening procedures (see, for example, Maniatis, *Molecular Cloning: A Laboratory Manual* (2nd Ed'n, 1989, Cold Spring Harbor, N.Y.)

B. MR-1 Sequence Characterization.

The complete coding sequence for the MR-1 cDNA is described in SEQ ID NO. 1 and is represented schematically in FIG. 1. The full length DNA sequence encodes a polypeptide chain about 516 amino acids in length that is glycosylated under standard physiological conditions. In FIG. 1 the first and second stippled regions represent the signal peptide sequence and the transmembrane domain, respectively. The signal peptide sequence, corresponding essentially to residues 1–24 of Seq.ID No. 1, is apparently 24 amino acids in length, the cleavage site being determined by the method of von Heijne (1986) *Nucleic Acids Research* 14:4683–4691.) The transmembrane region, corresponding essentially to residues 148–172 of Seq. ID No. 1, is rich in hydrophobic residues and is sufficient to span the cellular membrane one time. The open region corresponding essentially to residues 25–147 of Seq. ID No. 1 corresponds to the extracellular domain of the protein. This region is rich in cysteines, represented in the figure by vertical hatched lines, indicating that this region of the polypeptide chain likely is highly disulfide bonded. This region, which constitutes the ligand binding domain, shares little or no amino acid homology with the corresponding sequences of the TGFβ, activin or daf-1 receptor sequences (e.g., less than 26% amino acid identity.) Three possible glycosylation sites occur in this region, the positions being indicated by diamonds in the figure. The crosshatched region, corresponding to residues 173–492 of Seq. ID No. 1, corresponds to the intracellular (cytoplasmic domain) which shares 30–67% amino acid identity with the intracellular serine/threonine kinase domains of the other known serine/threonine kinase containing molecules (see FIG. 3.)

EXAMPLE 2

MR Expression

A. General Considerations

MR DNA, or a synthetic form thereof, can be inserted, using conventional techniques well described in the art (see, for example, Maniatis (1989) *Molecular Cloning A Laboratory Manual*), into any of a variety of expression vectors and transfected into an appropriate host cell to produce recombinant MR, such as MR-1 polypeptide chains, including both full length and truncated forms thereof. Shortened sequences, for example, can be used for the production of soluble receptor fragments.

Useful host cells include *E. coli*, Saccharomyces, the insect/baculovirus cell system, myeloma cells, and various other mammalian cells. The full length form of the proteins of this invention preferably are expressed in mammalian cells, as disclosed herein. Soluble forms may be expressed from both mammalian or bacterial cell systems. The vector additionally may include various sequences to promote correct expression of the recombinant protein, including transcription promoter and termination sequences, enhancer sequences, preferred ribosome binding site sequences, preferred mRNA leader sequences, preferred protein processing sequences, preferred signal sequences for protein secretion, and the like. The DNA sequence encoding the gene of interest also may be manipulated to remove potentially inhibiting sequences or to minimize unwanted secondary structure formation. The recombinant morphogen receptor also may be expressed as a fusion protein. After being translated, the protein may be purified from the cells themselves or recovered from the culture medium. The DNA also may include sequences that aid in expression and/or purification of the recombinant protein. One useful sequence for example, is a hexa-His ($His_6$) sequence, which adds a histidine tail to anchor the protein to an IMAC Cu2+ column (see below.)

For example, the DNA encoding the extracellular domain may be inserted into a suitable expression vector for transformation into a prokaryote host such as *E. coli* or *B. subtilis*, to produce a soluble, morphogen binding fragment. The DNA may expressed directly or may be expressed as part of a fusion protein having a readily cleavable fusion junction. An exemplary protocol for prokaryote expression using MR-1 DNA is provided below. Recombinant protein is expressed in inclusion bodies and may be purified therefrom using the technology disclosed in U.S. Pat. No. 5,013,653, for example.

The DNA also may be expressed in a suitable mammalian host. Currently preferred hosts include fibroblast 3T3 cells, (e.g., NIH 3T3, from CRL 1658) COS (simian kidney ATCC, CRL-1650) or CHO (Chinese hamster ovary) cells (e.g., CHO-DXB11, from Lawrence Chasin, Columbia University, N.Y.). An exemplary protocol for mammalian cell expression of MR-1 DNA in 3T3 cells is provided below. Other useful eukaryotic cell systems include yeast cells, the insect/baculovirus system or myeloma cells.

B. MR-1 Expression in *E. coli*

The extracellular domain of MR-1 was expressed in *E.coli*. The MR-1 DNA sequence of Seq. ID No. 1 was mutagenized in vitro using a "mutagene" kit (BioRad Laboratories, Inc., Richmond) to introduce a methionine (ATG) just before the first serine of the extracellular ligand binding domain (residue 25 in ID No. 1), and to introduce a stop codon after amino acid 147. This mutant DNA form was then cloned into a standard commercially available expression vector, (e.g., pET 3a vector, Novagen, Inc. Wisconsin, opened at NcoI and BamH1), and transfected into a bacterial cell line (e.g., BL21 DE3 pLys S cells, Novagen, Inc.) and expressed using standard procedures well described in the art. See, for example, Studier et al., (1990) *Methods in Enzymology* 185:60–89. Proteins then were isolated from inclusion bodies using standard procedures: Cells were grown overnight in the presence of 1 mM IPTG, lysed, and inclusion bodies isolated by centrifugation. Proteins then were resolubilized and passed over a TSK300 gel filtration column to partially purify the protein. The protein can be further purified, if desired, by gel electrophoresis. This form of the protein was used as antigen material for antibody production (see below.)

C. MR-1 Expression in CHO Cells

To express the MR-1 protein, the MR-1 DNA is subcloned into an insertion site of a suitable, commercially available vector (e.g., pCDM8, Invitrogen, Inc. San Diego), along with suitable promoter/enhancer sequences and 3' termination sequences. A currently preferred promoter/enhancer sequence combination includes the CMV promoter (human cytomegalovirus (MIE) promoter) present, for example, on pCDM8, as well as the mammary tumor virus promoter (mMTV) boosted by the rous sarcoma virus LTR enhancer sequence (e.g., from Clontech, Inc., Palo Alto). Expression also may be further enhanced using transactivating enhancer sequences. The plasmid also preferably contains DHFR as an amplifiable marker, under SV40 early promoter control (ATCC #37148). Transfection, cell culturing, gene amplification and protein expression conditions are standard conditions, well known in the art, such as are described, for example in Ausubel et al., ed., *Current Protocols in Molecular Biology*, John Wiley & Sons, NY (1989). Briefly, transfected cells are cultured in medium containing 5–10% dialyzed fetal calf serum (FCS), and stably transfected high expression cell lines obtained by amplification subcloning and evaluated by standard Western and Northern blot. Southern blots also can be used to assess the state of integrated receptor sequences and the extent of their copy number amplification.

The expressed protein then is purified using standard procedures. A currently preferred methodology uses an affinity column, such as a ligand affinity column or an antibody affinity column, the bound material then washed, and receptor molecules selectively eluted in a gradient of increasing ionic strength. Alternatively, where a useful anchor sequence has been added to the DNA, such as a $(His)_6$ sequence, the column may be a standard affinity column such as $Cu^{2+}$ IMAC column. Here, for example, the cell culture media containing the recombinant protein is passed over a $Cu^{2+}$ IMAC column prepared with 25 mM imidazol. The bound protein then is washed with a compatible solution and eluted with EDTA, and the anchor sequence removed by a standard chemical or enzymatic procedure.

Mammalian cell expression is preferred where morphogen receptor expression on a cell surface is desired. For example, cell surface expression may be desired to test morphogen or morphogen analog binding specificity for a cell surface receptor under in vivo conditions. Cell surface expression also may be most efficacious for high flux screen assays as described below.

EXAMPLE 3

Morphogen Receptor Antibody Production

A. General Considerations

Recombinantly produced MR can be used to obtain antibodies capable of specifically binding the receptor molecules and useful in immunoassays and in the immunopurification of morphogen receptors and as described above. Using the ligand binding assays described below, antibodies may be obtained which specifically recognize and interact with the receptor binding domain, and may be useful as morphogen analogs as described in Example 8, below.

Polyclonal antibodies specific for a morphogen receptor of interest may be prepared as described below for MR-1. Each rabbit is given a primary immunization (e.g., 500 μg) of recombinantly-produced MR-1 protein or protein fragment (e.g., extracellular domain, "ECD") in 0.1% SDS mixed with 500 μl Complete Freund's Adjuvant. The antigen is injected intradermally at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until antibody against MR-1 is detected in the serum using a standard Western blot. Then, the rabbit is boosted monthly with 100 μg/ml of antigen and bled (15 ml per bleed) at days seven and ten after boosting.

Similarly, monoclonal antibody specific for a given morphogen receptor molecule of interest may be prepared as described below for MR-1: A mouse is given two injections of MR-1 protein or a protein fragment specific for MR-1. The protein preferably is recombinantly produced. Where it is desired that the antibody recognize an epitope on the morphogen binding surface an MR-1 fragment derived from the extracellular domain preferably is provided. The first injection contains 100 μg of MR-1 in complete Freund's adjuvant and is given subcutaneously. The second injection contains 50 μg of MR-1 in incomplete adjuvant and is given intraperitoneally. The mouse then receives a total of 230 μg of MR-1 in four intraperitoneal injections at various times over an eight month period. One week prior to fusion, the mouse is boosted intraperitoneally with MR-1 (e.g., 100 μg) and may be additionally boosted with an MR-1-specific peptide (e.g., corresponding to a portion of the extracellular domain) conjugated to bovine serum albumin with a suitable crosslinking agent. This boost can be repeated five days (IP), four days (IP), three days (IP) and one day (IV) prior to fusion. The mouse spleen cells then are fused to commercially available myeloma cells at a ratio of 1:1 using PEG 1500 (Boehringer Mannheim, Germany), and the fused cells plated and screened for MR-1-specific antibodies using MR-1 as antigen. The cell fusion and monoclonal screening steps readily are performed according to standard procedures well described in standard texts widely available in the art. (See, for example, *Guide to Protein Purification* Murray P. Deutscher, ed., Academic Press, San Diego, 1990.

B. MR-1 Antisera

MR-1 antiserum was obtained using recombinantly produced soluble MR-1 as antigen and the polyclonal antibody production protocol described above. Soluble MR-1 was expressed from a DNA fragment derived from bases 25 to 147 of Seq. ID No. 1, as described in Example 2B. Antiserum reacted specifically with both the *E. coli*-produced and CHO-produced MR-1 proteins as determined by Western blot.

EXAMPLE 4

Ligand Binding Assays

Ligand binding specificity is determined by evaluating the ability of a receptor molecule to bind a specific ligand, and the ability of that ligand to compete against itself and other molecules which bind the receptor. Useful ligands will have a binding affinity for a soluble morphogen receptor extracellular domain such that dissociation constant (Kd) is less than about $10^{-7}$M, preferably less than $10^{-8}$M. Related morphogens are expected to be able to bind with specificity to a single given receptor molecule, although likely with differing affinities. This ability to "crosstalk" is demonstrated by the fact that dpp and 60A, two drosophila morphogens, both induce bone formation in a rat endochondral bone formation assay, normally induced with OP-1 or BMP2 homodimers or mixtures thereof. dpp is believed to be the drosophila homolog of BMP2, and 60A is believed to be the drosophila homolog of OP-1. In addition, introduction of BMP4 into a dpp- drosophila mutant genome is thought to compensate for the dpp- mutation in developing flies.

Ligand binding specificity can be assayed as follows, essentially following standard protocols well described in the art and disclosed, for example, in Legerski et al. (1992) *Biochem. Biophys. Res. Comm* 183:672–679 and Frakar et al., (1978) *Biochem. Biophys. Res.Comm.* 80:849–857. In the ligand binding assays, a ligand having a known, quantifiable affinity for a morphogen receptor molecule of interest is labelled, typically by radioiodination ($^{125}$I) or by metabolic labelling, e.g., $^{35}$S, and aliquots of cells expressing the receptor on their surface are incubated with the labelled ligand, in the presence of various concentrations of unlabelled competitor ligand. In the assays described in Example 8, below, this competitor typically is the candidate morphogen analog or an aliquot from a broth or extract that may contain a candidate morphogen analog.

Briefly, cells expressing MR-1 on their cell surface are plated into 35 mM dishes and incubated for 48 hours in DMEM (Dulbecco's modified Eagle medium) plus 10% fetal calf serum. Purified morphogen, here, e.g., OP-1, 60A or dpp is iodinated with Na$^{125}$I by chloramin T oxidation, preferably having a specific activity of about 50–100 μCi/μg, essentially following the protocol of Frolik et al. (1984) *J. Biol. Chem.* 595:10995–11000. Labelled morphogen then is purified using standard procedures, e.g., chromatographically. Plated cells are then washed twice with physiologically buffered saline in the presence of 0.1% BSA, and incubated at 22° C. in the presence of BSA, buffer and labelled morphogen (1 ng) and various concentrations (e.g., 0–10 μg/ml) of unlabelled competitor, e.g., unlabelled morphogen or candidate ligand analogs. Following binding, cells are washed three times with cold buffer, solubilized in 0.5 ml of 0.5N NaOH, removed from the dish, and radioactivity determined by gamma or scintillation counter. Data then are expressed as percent inhibition, where 100% inhibition of specific binding is the difference between binding in the absence of competitor and binding in the presence of a 100-fold molar excess of unlabelled morphogen or candidate ligand. Binding parameters preferably are determined using a computer program such as LIGAND (Munsun et al. (1980) *Anal. Biochem.* 107:220–259.)

Where the receptor cell surface binding domain is to be provided as a soluble protein, the assay may be performed in solution, most readily as an immunoprecipitation assay. In currently preferred assays the receptor molecule is labelled and incubated with unlabelled morphogen or candidate morphogen analogs. Morphogen-specific antibody then is provided to the solution to precipitate the receptor-morphogen complex and the amount of labelled morphogen in the precipitated complex determined using standard detection means.

In the morphogen analog screening assays described in Example 8 below, the preferred protocol is a standard competition or radioimmunoassay (RIA). Here the morphogen is labelled and the relative binding affinity of a candidate ligand in a sample is measured by quantitating the ability of the candidate (unlabelled ligand analog) to inhibit binding of the labelled ligand (competitor morphogen) by the receptor. In performing the assay, fixed concentrations of receptor and labelled morphogen are incubated in the absence and presence of unknown samples containing candidate ligands. Sensitivity may be increased by preincubating the receptor with candidate ligand before adding the labelled morphogen. After the labelled competitor has been added, sufficient time is allowed for adequate competitor binding, and then free and bound labelled morphogen are separated, and one or the other is measured. Useful morphogen labels include radioactive labels and conjugated enzymes having high turnover numbers, such as horseradish peroxidase, alkaline phosphatase, or β-galactosidase, used in combination with chemiluminescent or fluorogenic substrates.

Morphogens useful in binding assays may tested include the mature protein forms complexed with their pro domains, mature protein forms alone, and truncated forms comprising essentially just the C-terminal active domain.

EXAMPLE 5

Chimeric Receptor Molecules

Chimeric MR molecules, e.g., comprising an MR-1 extracellular and transmembrane region and, for example, part or all of an intracellular domain from another, different morphogen receptor or an intracellular domain from a different cell surface molecule, may be constructed using standard recombinant DNA technology and/or an automated DNA synthesizer to construct the desired sequence. As will be appreciated by persons skilled in the art, useful junctions include sequences within the transmembrane region and/or sequences at the junction of either the intracellular or the extracellular domains. Also envisioned are chimers where the extracellular domain or the intracellular domains themselves are chimeric sequences.

Chimeric sequences are envisioned to be particularly useful in screening assays to determine candidate binding ligands (e.g., morphogen analogs, see below), where the non-MR-1 intracellular domain provides a suitable second messenger response system that is easy to detect. Potentially useful other second messenger response systems include those which, when activated, induce phosphoinositide hydrolysis, adenylate cyclase, guanylate cyclase or ion channels.

Chimeric receptor molecules have particular utility in gene therapy protocols. For example, a population of cells expressing a chimeric morphogen receptor molecule their surface and competent for expressing a desired phenotype may be implanted in a mammal at a particular tissue locus. By careful choice of the ligand binding domain used on these receptors a physician can administer to the individual a morphogen agonist capable of binding to the chimeric receptor alone and stimulating the proliferation and/or differentiation of the implanted cells without affecting endogenous cell populations.

EXAMPLE 6

Considerations for Identifying Other Morphogen Receptors in Nucleic Acid LIBRARIES Identification of MR-1 allows one to identify other morphogen receptor sequences in different species as well as in different tissues. The MR-1 sequence itself can be used as a probe or the sequence may be modified to account for a preferred codon bias (e.g., human codon bias.) Currently preferred sequences are those which encode the extracellular domain.

Probes based on the nucleic acid sequence of Seq. ID No. 1 can be synthesized on commercially available DNA synthesizers, e.g. Applied Biosystems model 381A, using standard techniques, e.g. Gait, *Oligonucleotide Synthesis: A Practical Approach*, (IRL Press, Washington D.C., 1984). It is preferable that the probes are at least 8–50 bases long, more preferably 18–30 bases long. Probes can be labeled in a variety of ways standard in the art, e.g. using radioactive, enzymatic or colormetric labels as described, for example, by Berent et al, (May/June 1985) *Biotechniques*: 208–220; and Jablonski et al, (1986) *Nucleic Acids Research* 14: 6115–6128.

Preferably, low stringency conditions are employed when screening a library for morphogen receptor sequences using a probe derived from MR-1. Preferred MR-1-specific probes are those corresponding to bases encoding the extracellular domain ("ECD"), or encoding a unique (nonhomologous) sequence within the cytoplasmic domain. Useful probes may be designed from bases 450–820, for example. The probe may be further modified to use a preferred species codon bias, e.g., a human codon bias, for example.

For example, for a probe of about 20–40 bases a typical prehybridization, hybridization, and wash protocol is as follows: (1) prehybridization: incubate nitrocellulose filters containing the denatured target DNA for 3–4 hours at 55° C. in 5×Denhardt's solution, 6×SSC (20×SSC consists of 175 g NaCl, 88.2 g sodium citrate in 800 ml $H_2O$ adjusted to pH. 7.0 with 10N NaOH), 0.1% SDS, and 100 µg/ml denatured salmon sperm DNA, (2) hybridization: incubate filters in prehybridization solution plus probe at 42° C. for 14–48 hours, (3) wash; three 15 minutes washes in 6×SSC and 0.1% SDS at room temperature, followed by a final 1–1.5 minutes wash in 6×SSC and 0.1% SDS at 55° C. Other equivalent procedures, e.g. employing organic solvents such as formamide, are well known in the art.

Alternatively, morphogen receptor-specific DNA can be amplified using a PCR methodology such as the one disclosed herein, to amplify approximately 500 base pair fragments. As for the hybridization screening probes described above, the primer sequences preferably are derived from sequences encoding the extracellular domain, or from unique sequences occurring in the intracellular domain. The primers disclosed herein also are envisioned to be useful.

The invention also provides means for isolating transcriptional regulatory elements, particularly those occurring 5' and 3' to the coding sequence, as well as other, nontranslated sequences affecting stability, processing, transcription, translation, and tissue specificity. For example, using a probe derived from the 5' terminus of the sequence of Seq. ID No. 1, upstream untranslated sequences can be obtained. Similarly, using a sequence derived from the 3' terminus, downstream untranslated sequences can be obtained.

EXAMPLE 7

Tissue Distribution of Morphogen Receptors

Determining the tissue distribution of morphogen receptors may be used to identify different morphogen receptors expressed in a given tissue, and to identify new, related receptor molecules, as well as to identify target tissues for specific morphogens under naturally occurring conditions. The morphogen receptor molecules (or their mRNA transcripts) readily are identified in different tissues using standard methodologies and minor modifications thereof in tissues where expression may be low. For example, protein distribution may be determined using standard Western blot analysis or immunodetection techniques, and antibodies specific to the morphogen receptor molecules of interest. Similarly, the distribution of morphogen receptor transcripts may be determined using standard Northern hybridization protocols and transcript-specific probes or by in situ hybridization.

Any probe capable of hybridizing specifically to a transcript, and distinguishing the transcript of interest from other related transcripts may be used. Because the morphogen receptors described herein likely share high sequence homology in their intracellular domains, the tissue distribution of a specific morphogen receptor transcript may best be determined using a probe specific for the extracellular domain of the molecule. For example, a particularly useful MR-1-specific probe sequence is one derived from a portion of the 5' coding sequence. The chosen fragment then is labelled using standard means well known and described in the art and herein.

Using these morphogen-specific probes, which may be synthetically engineered or obtained from cloned sequences, morphogen receptor transcripts can be identified in various tissues of various organisms, using standard methodologies well known to those having ordinary skill in the art. A detailed description of a suitable hybridization protocol is described in Ozkaynak, et al., (1991) *Biochem. Biophys. Res. Commn.* 179:116–123, and Ozkaynak, et al. (1992) *J Biol. Chem.* 267:25220–25227. Briefly, total RNA is prepared from various tissues (e.g., murine embryo and developing and adult liver, kidney, testis, heart, brain, thymus, stomach) by a standard methodologies such as by the method of Chomczynski et al. ((1987) *Anal. Biochem* 162:156–159) and described below. Poly (A)+RNA is prepared by using oligo (dT)-cellulose chromatography (e.g., Type 7, from Pharmacia LKB Biotechnology, Inc.). Poly (A)+RNA (generally 15 $\mu$g) from each tissue is fractionated on a 1% agarose/formaldehyde gel and transferred onto a Nytran membrane (Schleicher & Schuell). Following the transfer, the membrane is baked at 80° C. and the RNA is cross-linked under UV light (generally 30 seconds at 1 mW/cm$^2$). Prior to hybridization, the appropriate probe is denatured by heating. The hybridization is carried out in a lucite cylinder rotating in a roller bottle apparatus at approximately 1 rev/min for approximately 15 hours at 37° C. using a hybridization mix of 40% formamide, 5×Denhardts, 5×SSPE, and 0.1% SDS. Following hybridization, the non-specific counts are washed off the filters in 0.1×SSPE, 0.1% SDS at 50° C.

EXAMPLE 8

Morphogen Analog Screening Assays

The present invention is useful to determine whether a ligand, such as a known or putative drug, is capable of binding to and/or activating a morphogen cell surface receptor as described herein. Ligands capable of specific binding interaction with a given morphogen receptor are referred to herein as morphogen analogs and may be used for therapeutic and diagnostic applications. Some morphogen analogs will have the ability to stimulate morphogenetic activity in the cell, these are morphogen agonists. Others will have strong binding affinity but will not stimulate morphogenesis, these are morphogen antagonists. These analogs may be amino acid-based, or they may be composed of non-proteinaceous chemical structures.

Transfection of an isolated clone encoding a morphogen receptor into the cell systems described above provides an assay system for the ability of ligands to bind to and/or to activate the receptor encoded by the isolated DNA molecule. Transfection systems, such as those described above, are useful as living cell cultures for competitive binding assays between known or candidate drugs and ligands which bind to the receptor and compete with the binding of known morphogens, which are labeled by radioactive, enzymatic, spectroscopic or other reagents. Membrane preparations containing the receptor and isolated from transfected cells are also useful in these competitive binding assays. Alternatively, and currently preferred, purified receptor molecules can be plated onto a microtiter well surface, in a modification of a sandwich assay, e.g., as a competition assay, such as an RIA, described above. Finally, as described above, solution assays, and using only the receptor extracellular domain, also may be used to advantage in these assays. Functional assays of second messenger systems or their sequelae in transfection systems act as assays for binding affinity and efficacy in the activation of receptor function. Such a transfection system constitutes a "drug discovery system", useful for the identification of natural or synthetic compounds with potential for drug development that can be further modified or used directly as therapeutic compounds to activate or inhibit the natural functions of the receptor encoded by the isolated DNA molecule.

Two approaches to identifying morphogen receptor binding analogs typically are practiced in the art: high flux screens and rational design of ligand mimetics. High flux screens typically screen naturally sourced materials or chemical banks for their ability to bind a protein of interest, here, the receptor. Typically, compounds are obtained from a range of sources, e.g., chemical banks, microbial broths, plant and animal extracts, and the like. In a high flux screen typically, purified receptor is plated onto a microtiter well surface and a standard volume of a sample solution to be tested then is added. Also added is a standard volume having a known quantity of a purified ligand known to bind the receptor with specificity. Preferably the ligand is labelled with a substance that is readily detectable by automated means (e.g., radiolabel, chromophoric, enzymatic or spectroscopic label.) The wells then are washed and the amount of label remaining after washing or the amount of label remaining associated with the receptor then is detected. Positive scores are identified by the ability of the test substance to prevent interaction of the labelled ligand with the receptor. Where MR-1 is the receptor, useful ligands for labelling include OP-1, 60A and DPP. High flux screens exploit both the high degree of specificity of the labelled ligand for its receptor, as well as high throughput capacity of computer driven robotics and computer handling of data. Candidate analogs identified in this manner, then can be analyzed structurally and this information used to design and to synthesize analogs having enhanced potency, increased duration of action, increased selectivity and reduced side effects. Candidates also can be used in a rational design program as described below. Finally, candidate analogs also can be tested to determine morphogenetic effect, if any, as described below.

The second approach to the identification of morphogen analogs uses a rational design approach to create molecules capable of mimicking the binding effect of morphogens with their receptors. Here the relevant structure for receptor binding is analyzed to identify critical sequences and structures necessary for binding activity and this information can be used to design and synthesize minimal size morphogen analogs. As for candidate compounds in the high flux assay, design candidates can be tested for ligand activity as described above.

Antibodies capable of interacting specifically with the morphogen receptor and competing with morphogen binding also may be used as morphogen analogs. Antibodies may be generated as described above.

Morphogen analogs may be evaluated for their ability to mimic morphogens or to inhibit morphogens (e.g., morphogen agonists or antagonists) by monitoring the effect of the analogs on cells bearing the appropriate morphogen receptors. Morphogen agonists are anticipated to have utility in any application where tissue morphogenesis is desired, such as in the regeneration of damaged tissue resulting from mechanical or chemical trauma, degenerative diseases, tissue destruction resulting from chronic inflammation, cirrhosis, inflammatory diseases, cancer and the like, and in the regeneration of tissues, organs and limbs. Morphogen antagonists are envisioned to have utility in applications where tissue morphogenesis is to be limited as, for example, in the treatment of malignant transformations including, but not limited to, osteosarcomas and Paget's disease.

For example, morphogens are known to preferentially induce differentiation of progenitor cells, including embryonic mesenchymal cells and primary osteoblasts (see, for example, PCT US92/07432 now published as WO 93/05751, the disclosure of which is incorporated herein by reference.) As one example, morphogen analogs can be tested for their ability to induce differentiation of primary osteoblasts, by measuring the ability of these analogs to induce production of alkaline phosphatase, PTH-mediated cAMP and osteocalcin, all of which are induced when primary osteoblasts are exposed to OP-1, 60A or DPP.

Briefly, the assays may be performed as follows. In this and all examples involving osteoblast cultures, rat osteoblast-enriched primary cultures preferably are used. Although these cultures are heterogeneous in that the individual cells are at different stages of differentiation, the culture is believed to more accurately reflect the metabolism and function of osteoblasts in vivo than osteoblast cultures obtained from established cell lines. Unless otherwise indicated, all chemicals referenced are standard, commercially available reagents, readily available from a number of sources, including Sigma Chemical, Co., St. Louis; Calbiochem, Corp., San Diego and Aldrich Chemical Co., Milwaukee.

Rat osteoblast-enriched primary cultures are prepared by sequential collagenase digestion of newborn suture-free rat calvaria (e.g., from 1–2 day-old animals, Long-Evans strain, Charles River Laboratories, Wilmington, Mass.), following standard procedures, such as are described, for example, in Wong et al., (1975) PNAS 72:3167–3171. Rat osteoblast single cell suspensions then are plated onto a multi-well plate (e.g., a 24 well plate) at a concentration of 50,000 osteoblasts per well in alpha MEM (modified Eagle's medium, Gibco, Inc., Long Island) containing 10% FBS (fetal bovine serum), L-glutamine and penicillin/streptomycin. The cells are incubated for 24 hours at 37° C., at which time the growth medium is replaced with alpha MEM containing 1% FBS and the cells incubated for an additional 24 hours so that the cells are in serum-deprived growth medium at the time of the experiment.

Alkaline Phosphatase Induction of Osteoblasts

The cultured cells in serum-free medium are incubated with morphogen (e.g., OP-1), morphogen analog or a negative control, using a range of concentrations. For example, 0.1, 1.0, 10.0, 40.0 or 80.0 ng OP-1/ml medium typically are used. 72 hours after the incubation period the cell layer is extracted with 0.5 ml of 1% Triton X-100. The resultant cell extract then, is centrifuged, and 100 $\mu$l of the extract is added to 90 $\mu$l of paranitrosophenylphospate (PNPP)/glycerine mixture and incubated for 30 minutes in a 37° C. water bath and the reaction stopped with 100 $\mu$l NaOH. The samples then are run through a plate reader (e.g., Dynatech MR700 plate reader, and absorbance measured at 400 nm, using p-nitrophenol as a standard) to determine the presence and amount of alkaline phosphatase activity. Protein concentrations are determined by the Biorad method. Alkaline phosphatase activity is calculated in units/$\mu$g protein, where 1 unit=1 nmol p-nitrophenol liberated/30 minutes at 37° C. OP-1 induces a five-fold increase in the specific activity of alkaline phosphate by this method. Agonists are expected to have similar induction effects. Antagonists should inhibit or otherwise interfere with morphogen binding, and diminished alkaline phosphatase induction should result when the assay is performed with an antagonist in the presence of a limiting amount of morphogen.

Induction of PTH-Mediated cAMP.

The effect of a morphogen analog on parathyroid hormone-mediated CAMP production in rat osteoblasts in vitro may be demonstrated as follows.

Rat osteoblasts are prepared and cultured in a multiwell plate as described above. The cultured cells then are divided into three groups: (1) wells which receive, for example, 1.0, 10.0 and 40.0 ng OP-1/ml medium); (2) wells which receive the candidate analog at various concentration ranges; and (3) a control group which receives no additional factors. The plate is then incubated for another 72 hours. At the end of the 72 hours the cells are treated with medium containing 0.5% bovine serum albumin (BSA) and 1mM 3-isobutyl-1-methylxanthine for 20 minutes followed by the addition into half of the wells of human recombinant parathyroid hormone (hPTH, Sigma, St. Louis) at a concentration of 200 ng/ml for 10 minutes. The cell layer then is extracted from each well with 0.5 ml of 1% Triton X-100. The cAMP levels then are determined using a radioimmunoassay kit (e.g., Amersham, Arlington Heights, Ill.). OP-1 doubles cAMP production in the presence of PTH. Agonists are expected to have similar induction effects. Antagonists are expected to inhibit or otherwise interfere with morphogen binding, and diminished cAMP production should result when the assay is performed with an antagonist in the presence of limiting the amount of morphogen.

Induction of Osteocalcin Production

Osteocalcin is a bone-specific protein synthesized by osteoblasts which plays an integral role in the rate of bone mineralization in vivo. Circulating levels of osteocalcin in serum are used as a marker for osteoblast activity and bone formation in vivo. Induction of osteocalcin synthesis in osteoblast-enriched cultures can be used to demonstrate morphogenic efficacy in vitro.

Rat osteoblasts are prepared and cultured in a multi-well plate as above. In this experiment the medium is supplemented with 10% FBS, and on day 2, cells are fed with fresh medium supplemented with fresh 10 mM $\beta$-glycerophosphate (Sigma, Inc.). Beginning on day 5 and twice weekly thereafter, cells are fed with a complete mineralization medium containing all of the above components plus fresh L(+)-ascorbate, at a final concentration of 50 $\mu$g/ml medium. Morphogen or morphogen analog then is added to the wells directly, e.g., in 50% acetonitrile (or 50% ethanol) containing 0.1% trifluoroacetic acid (TFA), at no more than 5 $\mu$l morphogen/ml medium. Control wells receive solvent vehicle only. The cells then are re-fed and the conditioned medium sample diluted 1:1 in standard radioimmunoassay buffer containing standard protease inhibitors and stored at –20° C. until assayed for osteocalcin. Osteocalcin synthesis is measured by standard radioimmunoassay using a commercially available osteocalcin-specific antibody and can be confirmed by Northern blot analysis to calculate the amount of osteocalcin mRNA produced in the presence and absence of OP-1 or morphogen analog. OP-1 induces a dose-dependent increase in osteocalcin production (5-fold increase using 25 ng of OP-1 protein/ml), and a 20-fold increase in osteocalcin mRNA. Agonists are expected to have similar induction effects; antagonists are expected to inhibit or otherwise interfere with morphogen binding, thereby substantially interfering with osteocalcin induction in the presence of a limiting amount of morphogen.

Mineralization is determined on long term cultures (13 day) using a modified von Kossa staining technique on fixed cell layers: cells are fixed in fresh 4% paraformaldehyde at 23° C. for 10 min, following rinsing cold 0.9% NaCl. Fixed cells then are stained for endogenous alkaline phosphatase at pH 9.5 for 10 min, using a commercially available kit (Sigma, Inc.) Purple stained cells then are dehydrated with methanol and air dried. After 30 min incubation in 3% $AgNO_3$ in the dark, $H_2O$-rinsed samples are exposed for 30 sec to 254 nm UV light to develop the black silver-stained phosphate nodules. Individual mineralized foci (at least 20 μm in size) are counted under a dissecting microscope and expressed as nodules/culture. OP-1 induces a 20-fold increase in initial mineralization rate. Agonists are expected to have similar induction effects; antagonists are expected to inhibit or otherwise interfere with morphogen binding, thereby inhibiting mineralization induction in the presence of a limiting amount of morphogen.

EXAMPLE 9

Screening Assay for Compounds Which Alter Endogenous Morphogen Receptor Levels

Candidate compound(s) which may be administered to affect the level of a given endogenous morphogen receptor may be found using the following screening assay, in which the level of morphogen receptor production by a cell type which produces measurable levels of the receptor is determined by incubating the cell in culture with and without the candidate compound, in order to assess the effects of the compound on the cell. This can be accomplished by detection of the morphogen receptor either at the protein or RNA level. The protocol is based on a procedure for identifying compounds which alter endogenous levels of morphogen expression, a detailed description also may be found in PCT US92/07359 (published as WO 93/05172), incorporated herein by reference.

Cell cultures of kidney, adrenals, urinary bladder, brain, or other organs, may be prepared as described widely in the literature. For example, kidneys may be explanted from neonatal or new born or young or adult rodents (mouse or rat) and used in organ culture as whole or sliced (1–4 mm) tissues. Primary tissue cultures and established cell lines, also derived from kidney, adrenals, urinary, bladder, brain, mammary, or other tissues may be established in multiwell plates (6 well or 24 well) according to conventional cell culture techniques, and are cultured in the absence or presence of serum for a period of time (1–7 days). Cells may be cultured, for example, in Dulbecco's Modified Eagle medium (Gibco, Long Island, N.Y.) containing serum (e.g., fetal calf serum at 1%–10%, Gibco) or in serum-deprived medium, as desired, or in defined medium (e.g., containing insulin, transferrin, glucose, albumin, or other growth factors).

Cell samples for testing the level of morphogen receptor production are collected periodically and evaluated for receptor production by immunoblot analysis (Sambrook et al., eds., 1989, Molecular Cloning, Cold Spring Harbor Press, Cold Spring Harbor, N.Y.), or, alternatively, a portion of the cell culture itself can be collected periodically and used to prepare polyA+RNA for RNA analysis. To monitor de novo receptor synthesis, some cultures are labeled according to conventional procedures with an $^{35}S$-methionine/$^{35}S$-cysteine mixture for 6–24 hours and then evaluated to quantitate receptor synthesis by conventional immunoassay methods. Alternatively, anti-receptor antibodies may be labelled and incubated with the cells or cell lysates, and the bound complexes detected and quantitated by conventional means, such as those described herein-above. Northern blots may be performed using a portion of the morphogen receptor coding sequence to create hybridization probes, and following the RNA hybridization protocol described herein.

EXAMPLE 10

General Morphogen Analog Formulation/ Administration Considerations

The morphogen analogs identified using the methodology described herein may be provided to an individual by any suitable means, preferably directly or systemically, e.g., parenterally or orally. Where the morphogen analog is to be provided directly (e.g., locally, as by injection, to a desired tissue site), or parenterally, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the analog preferably comprises part of an aqueous solution. The solution preferably is physiologically acceptable so that in addition to delivery of the desired morphogen to the patient, the solution does not otherwise adversely affect the patient's electrolyte and volume balance. The aqueous medium for the morphogen analog thus may comprise normal physiologic saline (0.9% NaCl, 0.15M), pH 7–7.4 or other pharmaceutically acceptable salts thereof.

Useful solutions for oral or parenteral administration may be prepared by any of the methods well known in the pharmaceutical art, described, for example, in *Remington's Pharmaceutical Sciences*, (Gennaro, A., ed.), Mack Pub., 1990. Formulations may include, for example, polyalkylene glycols such as polyethylene glycol, oils of vegetable origin, hydrogenated naphthalenes, and the like. Formulations for direct administration, in particular, may include glycerol and other compositions of high viscosity. Biocompatible, preferably bioresorbable polymers, including, for example, hyaluronic acid, collagen, tricalcium phosphate, polybutyrate, polylactide, polyglycolide and lactide/glycolide copolymers, may be useful excipients to control the release of the morphogen in vivo.

Other potentially useful parenteral delivery systems for these morphogen analogs include ethylene-vinyl acetate copolymer particles, osmotic pumps, implantable infusion systems, and liposomes. Formulations for inhalation administration may contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally.

Alternatively, the morphogens described herein may be administered orally.

The morphogen analogs also may be associated with means for targeting the analog to a desired tissue. For example, tetracycline and diphosphonates (bisphosphonates) are known to bind to bone mineral, particularly at zones of bone remodeling, when they are provided systemically in a mammal. Accordingly, these molecules may be included as useful agents for targeting analogs to bone tissue. Alternatively, an antibody or other binding protein that interacts specifically with a surface molecule on the desired target tissue cells also may be used. Such targeting molecules further may be covalently associated to the morphogen analog e.g., by chemical crosslinking, or by using standard genetic engineering means to create, for example, an acid labile bond such as an Asp-Pro linkage.

Useful targeting molecules may be designed, for example, using the single chain binding site technology disclosed, for example, in U.S. Pat. No. 5,091,513.

Finally, morphogen analogs may be administered alone or in combination with other molecules known to have a beneficial effect on tissue morphogenesis, including molecules capable of tissue repair and regeneration and/or inhibiting inflammation. Examples of useful cofactors for stimulating bone tissue growth in osteoporotic individuals, for example, include but are not limited to, vitamin $D_3$, calcitonin, prostaglandins, parathyroid hormone, dexamethasone, estrogen and IGF-I or IGF-II. Useful cofactors for nerve tissue repair and regeneration may include nerve growth factors. Other useful cofactors include symptom-alleviating cofactors, including antiseptics, antibiotics, antiviral and antifungal agents and analgesics and anesthetics.

Morphogen analogs further can be formulated into pharmaceutical compositions by admixture with pharmaceutically acceptable nontoxic excipients and carriers. As noted above, such compositions may be prepared for parenteral administration, particularly in the form of liquid solutions or suspensions; for oral administration, particularly in the form of tablets or capsules; or intranasally, particularly in the form of powders, nasal drops or aerosols. Where adhesion to a tissue surface is desired the composition may include the morphogen dispersed in a fibrinogen-thrombin composition or other bioadhesive such as is disclosed, for example in PCT US91/09275 (published as WO 92/10567), the disclosure of which is incorporated herein by reference. The composition then may be painted, sprayed or otherwise applied to the desired tissue surface.

The compositions can be formulated for parenteral or oral administration to humans or other mammals in therapeutically effective amounts, e.g., amounts which provide appropriate concentrations of the analog to target tissue for a time sufficient to induce the desired effect.

Where the analog is to be used as part of a transplant procedure, it may be provided to the living tissue or organ to be transplanted prior to removal of tissue or organ from the donor. The analog may be provided to the donor host directly, as by injection of a formulation comprising the analog into the tissue, or indirectly, e.g., by oral or parenteral administration, using any of the means described above.

Alternatively or, in addition, once removed from the donor, the organ or living tissue may be placed in a preservation solution containing the morphogen analog. In addition, the recipient also preferably is provided with the analog just prior to, or concomitant with, transplantation. In all cases, the analog may be administered directly to the tissue at risk, as by injection to the tissue, or it may be provided systemically, either by oral or parenteral administration, using any of the methods and formulations described herein and/or known in the art.

Where the morphogen analog comprises part of a tissue or organ preservation solution, any commercially available preservation solution may be used to advantage. For example, useful solutions known in the art include Collins solution, Wisconsin solution, Belzer solution, Eurocollins solution and lactated Ringer's solution. Generally, an organ preservation solution usually possesses one or more of the following properties: (a) an osmotic pressure substantially equal to that of the inside of a mammalian cell,(solutions typically are hyperosmolar and have K+ and/or Mg++ ions present in an amount sufficient to produce an osmotic pressure slightly higher than the inside of a mammalian cell); (b) the solution typically is capable of maintaining substantially normal ATP levels in the cells; and (c) the solution usually allows optimum maintenance of glucose metabolism in the cells. Organ preservation solutions also may contain anticoagulants, energy sources such as glucose, fructose and other sugars, metabolites, heavy metal chelators, glycerol and other materials of high viscosity to enhance survival at low temperatures, free oxygen radical inhibiting and/or scavenging agents and a pH indicator. A detailed description of preservation solutions and useful components may be found, for example, in U.S. Pat. No. 5,002,965, the disclosure of which is incorporated herein by reference.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. The preferred dosage of drug to be administered also is likely to depend on such variables as the type and extent of tissue loss or defect, the overall health status of the particular patient, the relative biological efficacy of the compound selected, the formulation of the compound, the presence and types of excipients in the formulation, and the route of administration. In general terms, the morphogen analogs of this invention may be provided to and individual where typical dose ranges are from about 10 ng/kg to about 1 g/kg of body weight per day; a preferred dose range being from about 0.1 µg/kg to 100 mg/kg of body weight. No obvious morphogen-induced pathological lesions are induced when mature morphogen (e.g., OP-1, 20 µg) is administered daily to normal growing rats for 21 consecutive days. Moreover, 10 µg systemic injections of morphogen (e.g., OP-1) injected daily for 10 days into normal newborn mice does not produce any gross abnormalities.

Finally, morphogen receptor ligand binding antagonists may be identified as described herein having utility as insecticidal agents. Specifically, MR-1 may be used as the receptor to identify receptor binding ligand as described herein antagonists capable of interfering with normal insect development. Useful morphogen antagonists may be combined with one or more excipients useful in insecticide formulations. Soluble forms of an insect-specific morphogen receptor may be useful. Those skilled in the art will appreciate that binding specificity is critical. Preferred binding affinities have a Kd less than $10^{-9}$M, preferably less than $10^{-10}$M.

Other Embodiments

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A purified polypeptide encoded by a DNA shown in SEQ ID NO: 1, or a allelic or species variant thereof, wherein said polypeptide has binding specificity for OP-1 or BMP2 while not significantly binding to TGF-β or activin and wherein the polypeptide is about 500 amino acids and has a molecular weight of about 58–90 kDa.

2. A purified polypeptide comprising amino acids 25–247 of SEQ ID NO: 2 or a allelic or species variant thereof, wherein said polypeptide has binding specificity for a morphogen selected from the group consisting of OP-1 or BMP2 while not significantly binding to TGF-β or activin and wherein the polypeptide is about 500 amino acids and has a molecular weight of about 58–90 kDa.

3. A purified polypeptide comprising amino acids 25–516 of SEQ ID NO: 2 or a allelic or species variant thereof, wherein said polypeptide has binding specificity for a morphogen selected from the group consisting of OP-1 or BMP2 while not significantly binding to TGF-β or activin and wherein the polypeptide is about 500 amino acids and has a molecular weight of about 58–90 kDa.

4. A polypeptide encoded by a nucleic acid that can be isolated by amplification with a first and a second nucleic acid primer, wherein said primers have sequences selected from the group consisting of SEQ ID NO: 4, SEQ ID NO: 5, SEQ ID NO: 6, or SEQ ID NO: 7, and wherein said polypeptide has binding specificity for a morphogen selected from the group consisting of OP-1 or BMP2 while not significantly binding to TGF-β or activin and wherein the polypeptide is about 500 amino acids and has a molecular weight of about 58–90 kDa.

5. The polypeptide of claim 4, wherein said primer comprise degenerate sequences.

6. The polypeptide of claim 4, wherein sequence of said primer comprise a species codon bias.

7. The polypeptide of claim 6, wherein said species codon bias is a human codon bias.

* * * * *